United States Patent [19]

Rault et al.

[11] Patent Number: 5,190,939
[45] Date of Patent: * Mar. 2, 1993

[54] PYRROLO (1,2-A) THIENO (3,2-F) (1,4) DIAZEPINES

[75] Inventors: Sylvain Rault, Moult; Michel Boulouard; Patrick Dallemagne, both of Caen; Max Robba, Paris; Béatrice Guardiola; Michelle Devissaguet, both of Neuilly Sur Seine, all of France

[73] Assignee: Adir et Compagnie, Courbevoie, France

[*] Notice: The portion of the term of this patent subsequent to Jul. 8, 2009 has been disclaimed.

[21] Appl. No.: 665,812

[22] Filed: Mar. 7, 1991

[30] Foreign Application Priority Data

Mar. 8, 1990 [FR] France ................. 90 02933

[51] Int. Cl.[5] ............. A61K 31/55; C07D 475/14
[52] U.S. Cl. ............................ 514/220; 540/496; 540/560
[58] Field of Search ............. 540/496, 560; 514/220

[56] References Cited

FOREIGN PATENT DOCUMENTS 0167919 1/1986 European Pat. Off. ............ 540/506

OTHER PUBLICATIONS

Novel Convenient Synthesis of 1,4-Diazepines, 6-Alkoxy-5,6-Dihydro-4H-Pyrrolo [1,2-a] Thieno [3,2-f-]-1,4-Diazepine-4-ones, S. Rault et al., Heterocycles (1979) 12 (8) pp. 1009-1011.

Pyrrolo [1,2-a] Thieno [3,2-f]-1,4-Diazepines. Novel Synthesis and X-Ray Analysis, S. Rault, et al., Tetrahedron Letters (1979)N° 7 pp. 643-644.

Synthesis of 4H-Pyrrolo [1,2-a] Thieno [3,2-f] [1,4] Diazepines, H. Fujimori, et al., Journal of Heterocyclic Chemistry (1977) 14 (2) pp. 235-240.

Synthése et étude de la 4H-Dihydro-5,6 Pyrrolo [1,2-a] Thieno [3,2-f] Diazepine-1,4, Comptes rendus de l'Académie des Science de Paris (1978) 287 pp. 117-120.

Primary Examiner—Robert T. Bond
Attorney, Agent, or Firm—Gordon W. Hueschen

[57] ABSTRACT

The invention relates to compounds of general formula I:

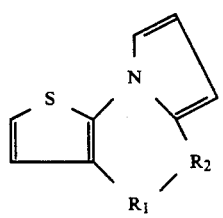

(I)

in which:
$R_1$ represents a radical of general formula $(Z_0)$, $(Z_1)$, $(Z_2)$, $(Z_3)$ or $(Z_4)$

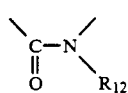
($Z_0$)

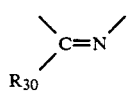

($Z_1$)

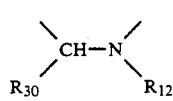

($Z_2$)

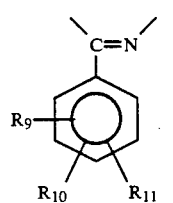

($Z_3$)

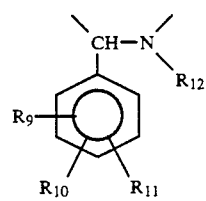

($Z_4$)

$R_2$ represents a methylene radical, a hydroxymethylene radical, a carbonyl radical or a radical of general formula $(Y_1)$, $(Y_2)$, $(Y_3)$ or $(Y_4)$:

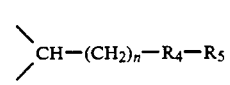

($Y_1$)

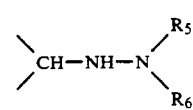

($Y_2$)

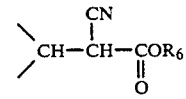

($Y_3$)

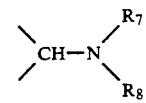

($Y_4$)

or, with $R_{12}$ and the nitrogen atom to which they are attached, forms a radical of general formula (W):

(Abstract continued on next page.)

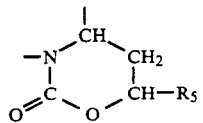
(W)
$R_3$, $R_4$, $R_5$, $R_6$, $R_7$, $R_8$, $R_9$, $R_{10}$, $R_{11}$, $R_{12}$ and n being as defined in the description, medicinal products containing the same and a method-of-treating metabolic ailments therewith.
18 Claims, No Drawings

PYRROLO (1,2-A) THIENO (3,2-F) (1,4) DIAZEPINES

The present invention relates to novel 4H-pyrrolo [1,2-a]thieno[3,2-f][1,4]diazepine, to their process of preparation and to the pharmaceutical compositions containing them.

Some 5,6-dihydro-4-oxo-4H-pyrrolo[1,2-a]thieno[3,2-f][1,4]diazepine compounds are described in the literature. (Heterocycles, 1979, Vol. 12, No. 8, pp. 1009–1011 and Tetrahedron Letters, 1979, No. 7, pp. 643–644). It is also known that some 6H-pyrrolo[1,2a]thieno[3,2-f][1,4]diazepine compounds might have antineoplastic properties (C. R. Acad. Sc. Paris, 1978, 287, pp. 117–120). 4-Phenyl-6H-pyrrolo[1,2-a]thieno[3,2-f][1,4]diazepine compounds are described in J. Heter. Chem., 1977, 14, No. 2, pp. 235–240.

The pyrrolo[1,2-a]thieno[3,2-f][1,4]diazepines of the Applicant are compounds of novel structure which possess advantageous pharmacological properties.

These compounds are endowed with exceptional antihypoxic properties, which are very advantageous in the treatment of cerebral aging, stroke and ischemic syndromes of any localization, acute, transient or progressive, through exerting their pharmacological properties with respect to the oxygen deficiency which accompanies these mishaps.

They are also potent CCK (cholecystokinin) antagonists. Diazepines which are cholecystokinin antagonists and which bind specifically to receptors for the latter, thereby enabling their use to be envisaged in the treatment of disorders of the central nervous system, stomach, intestine, pancreas or gall bladder and other CCK-dependent disorders, have already been described in European Patent 167,919. The compounds of the invention, while displaying activities equal to those of the most active compounds of the abovementioned European patent, are distinctly less toxic, so that their therapeutic index is better.

The compounds of the Applicant are also extremely advantageous by virtue of their metabolic effects, since they possess substantial hypoglycemic, hypocholesterolemic and hypotriglyceridemic properties, being, for example, much more active than clofibrate.

More specifically, the invention relates to the compounds of general formula (I):

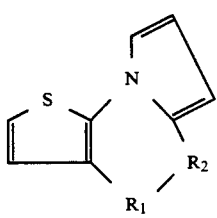  (I)

in which:
R$_1$ represents a radical of general formula (Z$_0$), (Z$_1$), (Z$_2$), (Z$_3$) or (Z$_4$)

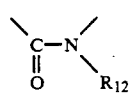  (Z$_0$)

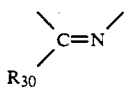  (Z$_1$)

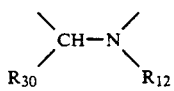  (Z$_2$)

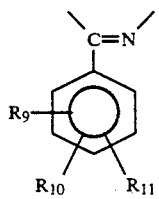  (Z$_3$)

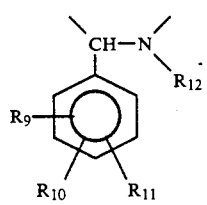  (Z$_4$)

in which formulae:
R$_3$ represents a hydrogen atom or a linear or branched alkyl radical having 1 to 6 carbon atoms, saturated or containing a double bond, R$_9$, R$_{10}$ and R$_{11}$, which may be identical or different, each represent a hydrogen atom, a halogen atom or an alkyl radical having 1 to 6 carbon atoms, R$_{12}$ represents a hydrogen atom or, with R$_2$ and the nitrogen atom to which they are attached, forms a radical of general formula (W):

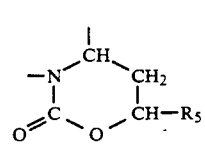  (W)

R$_2$ represents a methylene radical, a hydroxymethylene radical, a carbonyl radical or a radical of general formula (Y$_1$), (Y$_2$), (Y$_3$) or (Y$_4$):

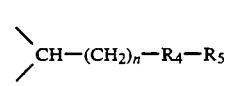  (Y$_1$)

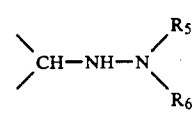  (Y$_2$)

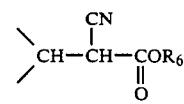  (Y$_3$)

-continued

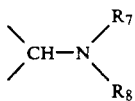 (Y4)

or, with $R_{12}$ and the nitrogen atom to which they are attached, forms a radical of general formula (W):

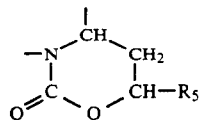 (W)

in which formulae:

$R_4$ represents an oxygen or sulfur atom, a carbonyl radical or a radical of general formula $(X_1)$, $(X_2)$, $(X_3)$ or $(X_4)$:

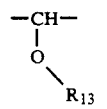 $(X_1)$

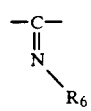 $(X_2)$

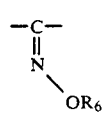 $(X_3)$

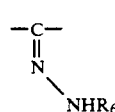 $(X_4)$ n is between 0 and 4 inclusive, $R_5$ represents a hydrogen atom, a linear or branched alkyl chain having 1 to 10 carbon atoms, optionally interrupted by one or more oxygen or sulfur atoms, a phenyl or benzoyl radical or an aralkyl radical having 7 to 11 carbon atoms (optionally substituted on the aromatic ring with one or more halogen atoms, linear or branched alkyl radicals having 1 to 6 carbon atoms, nitro radicals or linear or branched alkoxy radicals having 1 to 6 carbon atoms), a linear or branched carboxyalkyl radical having 2 to 7 carbon atoms, a linear or branched alkoxycarbonylalkyl radical having 3 to 10 carbon atoms, a linear or branched alkoxycarbonyl radical having 2 to 7 carbon atoms, a linear or branched carbamoylalkyl radical having 2 to 7 carbon atoms, a cycloalkyl radical having 3 to 7 carbon atoms or an unsaturated 5- to 7-membered ring-system comprising at least one hetero atom selected from nitrogen, sulfur and oxygen, a pyridylcarbonyl or pyrimidinylcarbonyl radical, a clofibroyl radical or a 6-hydroxy-2,5,7,8-tetramethylchroman-2-carbonyl radical, $R_6$ represents a hydrogen atom or a linear or branched alkyl radical having 1 to 6 carbon atoms, $R_7$ and $R_8$, which may be identical or different, each represent a hydrogen atom, a linear or branched alkyl radical having 1 to 6 carbon atoms, a phenyl radical or a phenylalkyl radical having 7 to 9 carbon atoms (optionally substituted on the aromatic ring with one or more halogen atoms or alkyl or alkoxy groups having 1 to 6 carbon atoms), or, together with the nitrogen atom to which they are attached, form a saturated or unsaturated 5- to 7-membered ring-system comprising 1 to 2 hetero atoms selected from nitrogen, oxygen and sulfur, optionally substituted with an alkylcarbonyl or alkoxycarbonyl group having 2 to 5 carbon atoms, $R_{13}$ represents a hydrogen atom, a linear or branched alkylcarbonyl radical having 2 to 6 carbon atoms or a benzoyl radical, with the provisos that:

when $R_1$ represents a radical of general formula $(Z_3)$, then $R_2$ cannot represent a methylene radical, when $R_1$ represents a radical of general formula $(Z_0)$ and $R_{12}$ represents a hydrogen atom, then $R_2$ cannot represent the following radicals:

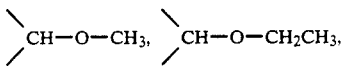

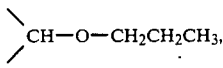

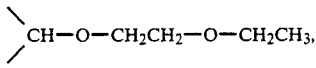

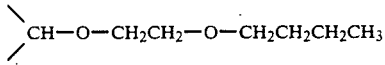

when $R_1$ represents a radical of general formula $(Z_0)$, $R_{12}$ represents a hydrogen atom and $R_2$ represents a radical of general formula $(Y_1)$ with $n=1$ and $R_4$ representing a carbonyl radical, then $R_5$ cannot represent a methyl, isopropyl or phenyl radical, when $R_1$ represents a radical of general formula $(Z_0)$ and $R_{12}$ represents a hydrogen atom, then $R_2$ cannot represent a carbonyl radical.

The present invention also encompasses a process for obtaining the compounds of general formula (I), wherein:

EITHER 3-cyano-2-(2-formyl-1-pyrrolyl)thiophene, the compound of formula (II):

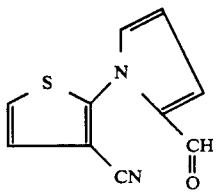 (II)

is reacted either with a methyl ketone of general formula (III):

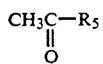 (III)

in which R₅ has the same meaning as in the compounds of general formula (I), in the presence of a strong inorganic base and hydrogen peroxide, so as to obtain the compounds of general formula (I$_A$):

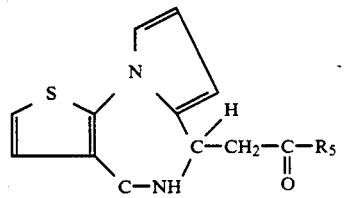 (I$_A$)

in which R₅ has the same meaning as in the compounds of general formula (I),
which are then:
either
subjected to the action of sodium borohydride, in solution in an alcoholic solvent, so as to obtain the compounds of general formula (I$_B$):

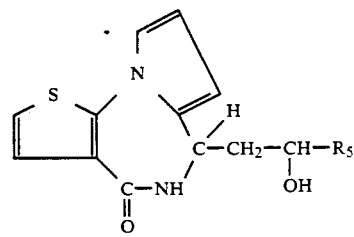 (I$_B$)

in which R₅ has the same meaning as in the compounds of general formula (I), which can optionally be subjected to the action of phosgene, in an aromatic organic solvent, in the heated state, to form the compounds of general formula (I$_C$):

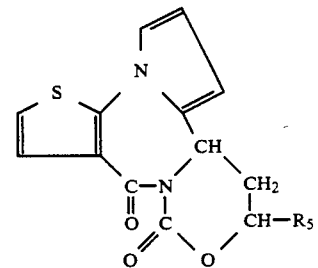 (I$_C$)

in which R₅ has the same meaning as in the compounds of general formula (I),
or be reacted with a compound of general formula (XI):

 R₁₃—Cl (XI)

in which R₁₃ has the same meaning as in the compounds of general formula (I), so as to obtain the compounds of general formula (I$_H$):

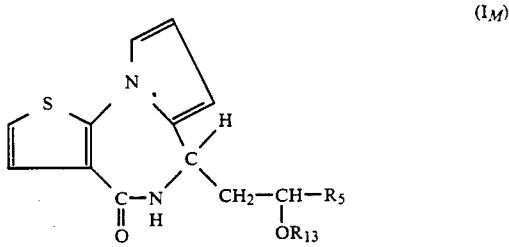 (I$_M$)

in which R₅ and R₁₃ have the same meaning as in the compounds of general formula (I),
or
condensed with a hydroxylamine derivative of general formula (IV):

 H₂N—O—R₆ (IV)

in which R₆ has the same meaning as in the compounds of general formula (I), to form the compounds of general formula (I$_D$):

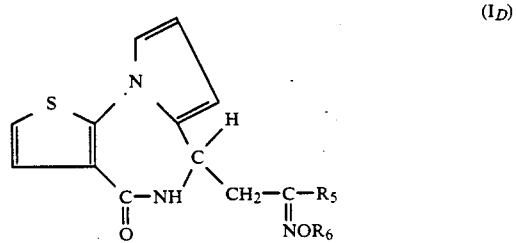 (I$_D$)

in which R₅ and R₆ have the same meaning as in the compounds of general formula (I),
or
condensed with a hydrazine compound of general formula (XII):

 H₂N—NH—R₆ (XII)

in which R₆ has the same meaning as in the compounds of general formula (I), so as to obtain the compounds of general formula (I$_N$):

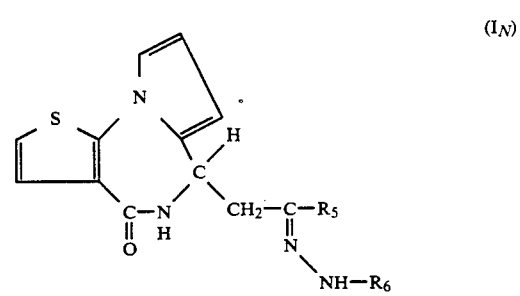 (I$_N$)

in which R₅ and R₆ have the same meaning as in the compounds of general formula (I),
or
with a primary alcohol or general formula (V):

 R₃OH (V)

in which R₃ has the same meaning as in the compounds of general formula (I), in the presence of a strong inorganic base and at a temperature of between 30° and 80° C., so as to obtain the compounds of general formula ($I_E$):

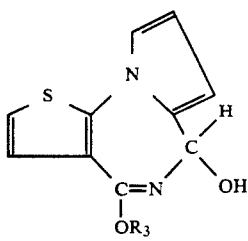

($I_E$)

in which $R_3$ has the same meaning as in the compounds of general formula (I), which is then subjected to the action of potassium permanganate, at room temperature, to form the compounds of general formula ($I_F$):

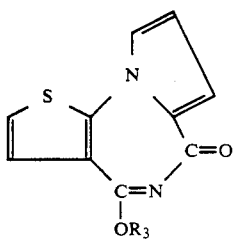

($I_F$)

in which $R_3$ has the same meaning as in the compounds of general formula (I), which can optionally be subjected to the action of sodium borohydride to obtain the compounds of general formula ($I_G$):

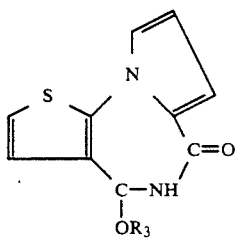

($I_G$)

in which $R_3$ has the same meaning as in the compounds of general formula (I),

OR 3-carbamoyl-2-(2-formyl-1-pyrrolyl)thiophene, the compound of formula (VI):

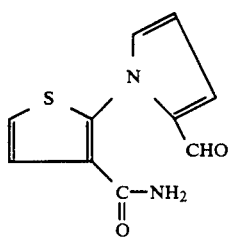

(VI)

is subjected
either
to the action of an amine of general formula (VII):

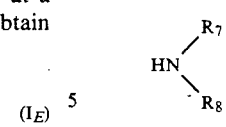

(VII)

in which $R_7$ and $R_8$ have the same meaning as in the compounds of general formula (I), so as to obtain the compounds of general formula ($I_H$):

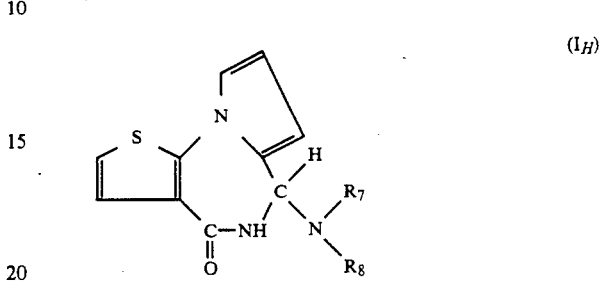

($I_H$)

in which $R_7$ and $R_8$ have the same meaning as in the compounds of general formula (I), which can optionally be subjected, in the case where $R_7$ and $R_8$, together with the nitrogen atom to which they are attached, form a morpholino radical, to the action of sodium borohydride, to obtain the compound of general formula (I) in which $R_2$ represents a methylene radical and $R_1$ a radical of general formula ($Z_0$) with $R_{12}=H$, or to the action of triethylamine in the presence of water and at room temperature to form the compound of general formula (I) in which $R_2$ represents a hydroxymethylene radical and $R_1$ a radical of formula ($Z_0$) with $R_{12}=H$, which is then:
either
reacted with an amine of general formula (VII), to form the compounds of general formula ($I_H$), or
condensed with a compound of general formula (VIII):

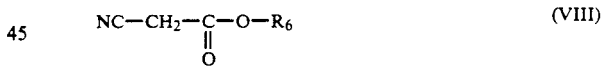

(VIII)

in which $R_6$ has the same meaning as in the compounds of general formula (I), in the presence of triethylamine, to form the compounds of general formula ($I_J$):

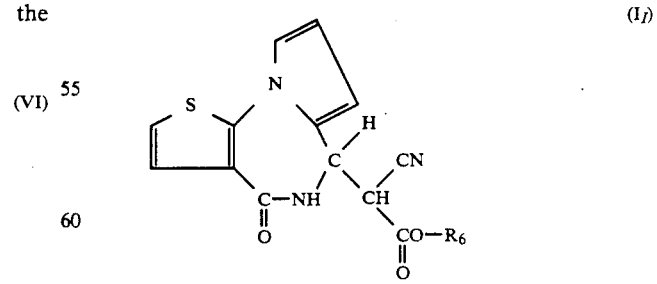

($I_J$)

in which $R_6$ has the same meaning as in the compounds of general formula (I), or
reacted with an alcohol of general formula (IX):

R₅OH (IX)

in which R₅ has the same meaning as in the compounds of general formula (I), in the heated state, to obtain the compounds of general formula (I_J):

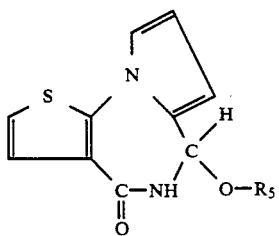

(I_J)

in which R₅ has the same meaning as in the compounds of general formula (I):
or
to the action of a compound of general formula (X):

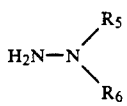

(X)

in which R₅ and R₆ have the same meaning as in the compounds of general formula (I), to form the compounds of general formula (I_K):

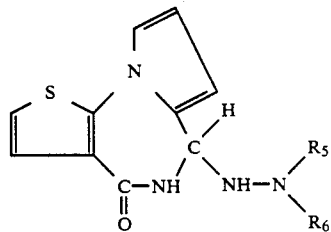

(I_K)

in which R₅ and R₆ have the same meaning as in the compounds of general formula (I),
or
to the action of an alcohol of general formula (IX), to form the compounds of general formula (I_J),
or
to the action of a thiol of general formula (XI):

R₅SH (XI)

in which R₅ has the same meaning as in the compounds of general formula (I), at room temperature, to form the compounds of general formula (I_L):

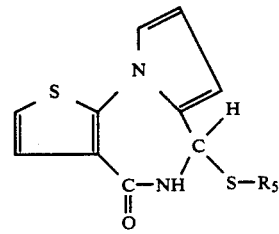

(I_L)

in which R₅ has the same meaning as in the compounds of general formula (I), which can optionally be subjected, in the case where R₅ represents a carboxyalkyl radical, to the action of triethylamine and a chloroformate and then to the action of gaseous ammonia to form the corresponding amides.

The compounds of general formulae (I_A) to (I_N) form part of the invention and are comprised within the compounds of general formula (I).

3-Cyano-2-(2-formyl-1-pyrrolyl)thiophene, the compound of formula (II), is an already known compound (Heterocycles, 1986, Vol. 24, (3), pp. 575–578).

The condensation of the compound of general formula (II) with the compounds of general formula (III) is performed in an aqueous-alcoholic mixture, in the heated state, in the presence of a strong inorganic base and hydrogen peroxide.

The reduction of the compounds of general formula (I_A) with sodium borohydride, with leads to the production of the compounds of general formula (I_B), is carried out in a low molecular weight primary alcohol at room temperature.

To obtain the compounds of general formula (I_C), the cyclization of the compounds of general formula (I_B) is carried out in the heated state, with phosgene, in an aromatic organic solvent such as, for example, toluene.

The compounds of general formula (I_D) are obtained from the compounds of general formula (I_A). The latter are dissolved in a low molecular weight alcohol. The compounds of general formula (IV) are then added in the presence of sodium acetate and the mixture is heated to reflux.

3-Carbamoyl-2-(2-formyl-1-pyrrolyl)thiophene, the compound of formula (VI), was prepared from the compound of formula (II) according to conventional methods.

The reaction of the compound of formula (VI) with the amines of general formula (VII) is performed in water at room temperature when the amines are present in excess in the reaction medium (10 times the requisite molar quantity), or in the heated state in acetonitrile when the quantities of the compounds (VI) and (VII) are equimolar.

To obtain the compounds of general formula (I_K), the reaction of the compounds of general formula (X) with the compound of formula (VI) is performed in water at a temperature of between 50° and 70° C. The end of the reaction is carried out at room temperature.

The compounds according to the invention, as well as their salts, are endowed with highly advantageous pharmacological properties. In effect, pharmacological tests in vivo showed that the compounds of the present invention exert a potent antihypoxic effect in animals.

During aging or following a stroke, increased frailty and cell vulnerability are physiopathological components of importance in the search for new treatments directed towards protecting the brain placed in the position of inability to respond to any further stress emanating from its environment.

Such a stress may be reproduced in the form of a defective oxygen supply, and for this reason, in terms of their consequences, there is a close analogy between hypoxia and cerebral aging.

The compounds of the present invention were tested for their capacity to prolong survival of the cerebral tissue during acute hypoxia in mice. The results of the tests demonstrated that the compounds of the invention have a very potent antihypoxic protective effect, and thus confirmed the great value of their use in therapy.

By clearly counteracting brain death during insufficiency of the oxygen supply, the compounds of the present invention exert a pronounced antihypoxic effect and are hence useful in the case of ischemic syndromes of any localization, acute, transient or progressive, since they exert their pharmacological properties with respect to the oxygen deficiency which accompanies these mishaps. Their pharmacological properties enable them to be applied in the correction of disorders linked to hypoxemia, for example during cerebral aging.

The affinity of the compounds of the invention for cholecystokinin receptors was studied by determining the median inhibitory concentration ($IC_{50}$) for the binding of iodine-125-labeled cholecystokinin to the receptors of rat pancreas plasma membranes and of guinea pig brain membranes. For the majority of the compounds of the invention, it was found that the ratio of the $IC_{50}$ for the brain receptors to the $IC_{50}$ for the pancreatic receptors is very high. This demonstrates that the compounds of the invention display better selectivity for the peripheral cholecystokinin receptors, and permit better treatment of the disorders dependent thereon, with fewer side effects.

The compounds of the invention are hence seen to be especially useful in human or veterinary therapy in the treatment of cholecystokinin-dependent stomach, intestine, pancreas and gall bladder disorders, such as, for example, pancreatitis, disorders of gastric or gall bladder motor function, ulcers and irritable colon syndrome. They also find their application in the treatment of pain, where appropriate of disorders dependent on the interaction of cholecystokinin with neuromediators of the central nervous system, such as, for example, neuroleptic disorders, Parkinson's disease, psychosis and tardive dyskinesia. The compounds of the invention are also useful for regulating the appetite.

The compounds of the invention also possess exceptional metabolic properties, being strongly hypolipemic, hypocholesterolemic and hypotriglyceridemic.

When given for 14 days to rats subjected to a hypercholesterolemic diet, they proved to be much more active (at least 30-fold) than clofibrate with respect to the lowering of the plasma triglyceride, cholesterol and HDL (high density lipoprotein)-cholesterol levels.

The toxicity was evaluated in male mice. The $LD_{50}$ of the compounds of the invention is greater than 1,500 mg/Kg (administered i.p.).

The compounds of general formula (I), as well as their addition salts with a pharmaceutically acceptable inorganic or organic acid such as, for example, hydrochloric, methanesulfonic, citric and maleic acids, may be made into pharmaceutical preparations according to generally known processes, such as, for example, into tablets, hard gelatin capsules, dragees, solutions for oral administration, injectable solutions, suspensions for oral administration, emulsions and suppositories.

Apart from non-toxic and pharmaceutically acceptable inert excipients such as, for example, distilled water, glucose, lactose, starch, talc, vegetable oils, ethylene glycol, and the like, these preparations can also contain preservatives, stabilizers, wetting agents, emulsifiers, and the like.

The compositions thereby obtained generally take the form of measured doses, and can contain, depending on the conditions treated and the patient's age and sex, from 0.1 to 100 mg of active principle. Depending on the circumstances, they may be administered orally, rectally or parenterally, at a dose of 0.1 to 100 mg from one to several times a day.

The examples which follow illustrate the invention and in no way limit the latter.

The $^1H$ NMR spectrometry characteristics are collated in Tables I to XIII.

EXAMPLE 1

5,6-dihydro-4-oxo-6-(2-oxo-1-pentyl)-4H-pyrrolo[1,2-a]thieno[3,2-f][1,4]diazepine A solution of 12 g (0.059 mole) of 3-cyano-2-(2-formyl-1-pyrrolyl)thiophene in a mixture of 200 ml of 2-pentanone, 200 ml of 6N sodium hydroxide and 15 ml of 33% hydrogen peroxide is heated to reflux for one hour. The ethanol and 2-pentanone are then removed under vacuum and the remainder of the reaction mixture is poured into 200 ml of cold water. The precipitate formed is drained, washed with water, dried and recrystallized.

Yield: 68%.

Melting point: 186° C. (Ethyl ether/acetone), yellow crystals.

|  | Elemental analysis: | | | |
|---|---|---|---|---|
|  | C % | H % | N % | S % |
| Theory | 62.49 | 5.59 | 9.72 | 11.10 |
| Found | 62.48 | 5.50 | 9.72 | 11.23 |

IR spectrum (KBr): NH bands at 3275 and 3170 cm$^{-1}$, CH bands at 3050, 2950, 2920 and 2870 cm$^{-1}$, C=O bands at 1705 (ketone) and 1640 cm$^{-1}$ (lactam), main bands at 1470, 1440, 1325, 1150, 1095, 795, 705 and 685 cm$^{-1}$.

EXAMPLE 2

6-(2-cyclopropyl-2-oxo-1-ethyl)-5,6-dihydro-4-oxo-4H-pyrrolo[1,2-a]thieno[3,2-f][1,4]diazepine This compound was prepared according to the process described in Example 1, but using cyclopropyl methyl ketone instead of 2-pentanone.

Yield: 57%.

Melting point: 200° C. (Ethyl ether/acetone), white crystals.

|  | Elemental analysis: | | | |
|---|---|---|---|---|
|  | C % | H % | N % | S % |
| Theory | 62.91 | 4.92 | 9.78 | 11.19 |
| Found | 62.87 | 4.93 | 9.81 | 11.05 |

IR spectrum (KBr): NH bands at 3270 and 3180 cm$^{-1}$, CH bands at 3120, 3090, 3050 and 2890 cm$^{-1}$, CO bands at 1685 and 1640 cm$^{-1}$, main bands at 1530, 1475, 1440, 1395, 1330, 1090, 910 and 735 cm$^{-1}$.

EXAMPLE 3

5,6-dihydro-4-oxo-6-[2-oxo-2-(phenethyl)ethyl]-4H-pyrrolo[1,2-a]thieno[3,2-f][1,4]diazepine This compound was prepared according to the process described in Example 1, but using benzyl acetone as a ketone.

Yield: 19%.

Melting point: 172° C. (Ethyl ether), white crystals.

| Elemental analysis: | | | |
|---|---|---|---|
| | C % | H % | N % | S % |
| Theory | 68.55 | 5.18 | 7.99 | 9.15 |
| Found | 68.22 | 5.36 | 7.90 | 8.85 |

IR spectrum (KBr): NH bands at 3270 and 3170 cm$^{-1}$, CH bands at 3050, 3020, 2920 and 2880 cm$^{-1}$, CO bands at 1710 and 1645 cm$^{-1}$, main bands at 1485, 1440, 1330, 1190, 1100 and 705 cm$^{-1}$.

EXAMPLE 4

5,6-dihydro-6-(4-methylphenacyl)-4-oxo-4H-pyrrolo[1,2-a]thieno[3,2-f][1,4]diazepine This compound was prepared according to the process described in Example 1, but using 4-methylacetophenone instead of 2-pentanone.
Yield: 44%.
Melting point: 190° C. (Ethyl ether), white crystals.

| Elemental analysis: | | | |
|---|---|---|---|
| | C % | H % | N % | S % |
| Theory | 67.84 | 4.79 | 8.33 | 9.53 |
| Found | 68.39 | 5.01 | 8.13 | 8.96 |

IR spectrum (KBr): NH band at 3320 cm$^{-1}$, CH bands at 3080, 3060, 3040 and 2920 cm$^{-1}$, CO band at 1670 cm$^{-1}$, main bands at 1485, 1435, 1325, 810, 705 and 685 cm$^{-1}$.

EXAMPLE 5

5,6-dihydro-6-(2-methylphenacyl)-4-oxo-4H-pyrrolo[1,2-a]thieno[3,2-f][1,4]diazepine This compound was prepared according to the process described in Example 1, but using ortho-acetyltoluene.
Yield: 44%.
Melting point: 180° C. (Ethyl ether), gray crystals.

| Elemental analysis: | | | |
|---|---|---|---|
| | C % | H % | N % | S % |
| Theory | 67.84 | 4.79 | 8.33 | 9.53 |
| Found | 67.72 | 4.82 | 8.44 | 9.43 |

IR spectrum (KBr): NH bands at 3270 and 3160 cm$^{-1}$, CH bands at 3040, 2920 and 2890 cm$^{-1}$, CO bands at 1680 and 1650 cm$^{-1}$, main bands at 1530, 1480, 1435, 1330, 1210, 1145, 985, 810, 765 and 720 cm$^{-1}$.

EXAMPLE 6

5,6-dihydro-6-(2,5-dimethoxyphenacyl)-4-oxo-4H-pyrrolo[1,2-a]thieno[3,2-f][1,4]diazepine The procedure is as in the previous example, but using 2,5-dimethoxyacetophenone.
Yield: 19%.
Melting point: 180° C. (Acetonitrile), white flocculent product.

| Elemental analysis: | | |
|---|---|---|
| | C % | H % | N % |
| Theory | 62.81 | 4.74 | 7.32 |
| Found | 62.75 | 4.76 | 7.34 |

IR spectrum (KBr): NH bands at 3260 and 3190 cm$^{-1}$, CH bands at 3050, 2930, 2900 and 2830 cm$^{-1}$, C=O band at 1675 cm$^{-1}$, main bands at 1490, 1410, 1220, 1035, 810 and 700 cm$^{-1}$.

EXAMPLE 7

6-(4-chlorophenacyl)-5,6-dihydro-4-oxo-4H-pyrrolo[1,2-a]thieno[3,2-f][1,4]diazepine This compound was prepared according to the process described in Example 1, but using 4-chloroacetophenone.
Yield: 24%.
Melting point: 224° C. (Ethanol), beige crystals.

| Elemental analysis: | | | |
|---|---|---|---|
| | C % | H % | N % | Cl % |
| Theory | 60.58 | 3.67 | 7.85 | 9.93 |
| Found | 61.14 | 3.66 | 7.53 | 10.49 |

IR spectrum (KBr): NH band at 3320 cm$^{-1}$, CH bands at 3080 and 2910 cm$^{-1}$, C=O bands at 1740 cm$^{-1}$ (acetone) and 1635 cm$^{-1}$ (lactam), main bands at 1580, 1480, 1430, 1320, 1210, 1090, 990 and 705 cm$^{-1}$.

EXAMPLE 8

5,6-dihydro-4-oxo-6-[2-oxo-2-(2-thienyl)ethyl]-4H-pyrrolo[1,2-a]thieno[3,2-f][1,4]diazepine The procedure is as in the previous example, but using 2-acetylthiophene.
Yield: 20%.
Melting point: 186° C. (Isopropanol), beige crystals.

| Elemental analysis: | | |
|---|---|---|
| | C % | H % | S % |
| Theory | 58.52 | 3.68 | 19.52 |
| Found | 57.91 | 3.91 | 18.90 |

IR spectrum (KBr): NH band at 3320 cm$^{-1}$, CH bands at 3080, 2960 and 2920 cm$^{-1}$, CO bands at 1655 cm$^{-1}$ and 1640 cm$^{-1}$, main bands at 1530, 1485, 1440, 1325, 1220, 1140, 860, 720 and 710 cm$^{-1}$.

EXAMPLE 9

5,6-dihydro-6-(4-fluorophenacyl)-4-oxo-4H-pyrrolo[1,2-a]thieno[3,2-f][1,4]diazepine This compound was prepared according to the process described in Example 1, but using 4-fluoroacetophenone.
Yield: 21%.
Melting point: 170° C. (Ethyl ether), beige crystals.

| Elemental analysis: | | | |
|---|---|---|---|
| | C % | H % | S % | F % |
| Theory | 63.51 | 3.84 | 9.41 | 5.58 |
| Found | 63.61 | 3.66 | 8.88 | 5.40 |

IR spectrum (KBr): NH band at 3320 cm$^{-1}$, C=O bands at 1670 cm$^{-1}$ (ketone) and 1640 cm$^{-1}$ (lactam), main bands at 1595 1485, 1440, 1330, 1215, 1000, 840 and 710 cm$^{-1}$.

EXAMPLE 10

5,6-dihydro-6-(2-furyl-2-oxoethyl)-4-oxo-4H-pyrrolo[1,2-a]thieno[3,2-f][1,4]diazepine The procedure is as in the previous example, but using 2-acetylfuran.

Yield: 19.6%.

| | Elemental analysis: | | |
|---|---|---|---|
| | C % | H % | S % |
| Theory | 61.53 | 3.87 | 10.26 |
| Found | 61.29 | 3.69 | 10.41 |

IR spectrum (KBr): NH band at 3180 cm$^{-1}$, CH bands at 3050 and 2920 cm$^{-1}$, C=O bands at 1670 cm$^{-1}$ (ketone) and 1640 cm$^{-1}$ (lactam), main bands at 1485, 1460, 1435, 1330, 1145, 995 and 725 cm$^{-1}$.

EXAMPLE 11

5,6-dihydro-6-(3,3-dimethyl-2-oxo-1-butyl)-4-oxo-4H-pyrrolo[1,2-a]thieno[3,2-f][1,4]diazepine This compound was prepared according to the process described in Example 1, starting with pinacolone.

After removal of the ethanol, the remainder of the reaction mixture is poured into 100 ml of water. The oily precipitate formed is extracted with ethyl ether. The ether phase is washed with water, dried over magnesium sulfate and taken down under vacuum. The pinacolone is then removed from the residue by washing with a petroleum ether/ethyl ether (50:50 v/v) mixture. The insoluble solid is drained, washed with water, dried and recrystallized.

Yield: 26%.

Melting point: 170° C. (Ethyl ether), beige crystals.

| | Elemental analysis: | | | |
|---|---|---|---|---|
| | C % | H % | N % | S % |
| Theory | 63.55 | 5.99 | 9.26 | 10.60 |
| Found | 62.20 | 5.72 | 8.80 | 10.41 |

IR spectrum (KBr): NH bands at 3260 and 3170 cm$^{-1}$, CH bands at 3110, 3060, 2980 and 2900 cm$^{-1}$, C=O bands at 1700 cm$^{-1}$ (ketone) and 1735 cm$^{-1}$ (lactam), main bands at 1485 1430, 1330, 1195, 1090, 830, 735 and 720 cm$^{-1}$.

EXAMPLE 12

5,6-dihydro-6-(2-hydroxypropyl)-4-oxo-4H-pyrrolo[1,2-a]thieno[3,2-f][1,4]diazepine 1.46 g of sodium borohydride are added in small portions to a solution of 2.5 g of 6-acetonyl-5,6-dihydro-4-oxo-4H-pyrrolo[1,2-a]thieno[3,2-f][1,4]diazepine in 200 ml of methanol, and the reaction mixture is then stirred at room temperature for 3 hours. The methanol is then removed under vacuum and the residual solid ground in 200 ml of water. The precipitate obtained is drained, washed with water, dried and recrystallized.

Yield: 80%.

Melting point: 171° C. (Ethyl ether), white crystal.

| | Elemental analysis: | | | |
|---|---|---|---|---|
| | C % | H % | N % | S % |
| Theory | 59.47 | 5.34 | 10.67 | 12.20 |
| Found | 59.42 | 5.28 | 10.72 | 12.08 |

IR spectrum (KBr): OH band at 3450 cm$^{-1}$, NH bands at 3260 and 3190 cm$^{-1}$, CH bands at 3040, 2960, 2920 and 2880 cm$^{-1}$, CO band at 1630 cm$^{-1}$, main bands at 1535, 1485, 1440, 1330, 1085, 885, 700 and 680 cm$^{-1}$.

EXAMPLE 13

5,6-dihydro-4-oxo-6-(2-hydroxy-1-pentyl)-4H-pyrrolo[1,2-a]thieno[3,2-f][1,4]diazepine This compound was prepared from the compound described in Example 1 and according to the process described in Example 12.

Yield: 80%.

Melting point: 188° C. (Isopropanol), yellow crystals.

| | Elemental analysis: | | | |
|---|---|---|---|---|
| | C % | H % | N % | S % |
| Theory | 62.04 | 6.24 | 9.64 | 11.04 |
| Found | 62.10 | 6.18 | 9.55 | 10.89 |

IR spectrum (KBr): OH band at 3440 cm$^{-1}$, NH bands at 3250 and 3170 cm$^{-1}$, CH bands at 3030, 2950, 2930, 2900 and 2860 cm$^{-1}$, CO band at 1630 cm$^{-1}$, main bands at 1530, 1480, 1440, 1335, 1090, 1025, 805, 705 and 690 cm$^{-1}$.

EXAMPLE 14

6-(2-cyclopropyl-2-hydroxyethyl)-5,6-dihydro-4-oxo-4H-pyrrolo[1,2-a]thieno[3,2-f][1,4]diazepine This compound was prepared from the compound of Example 2 according to the process described in Example 12.

Yield: 80%.

Melting point: 222° C. (Isopropanol), white crystals.

| | Elemental analysis: | | | |
|---|---|---|---|---|
| | C % | H % | N % | S % |
| Theory | 62.47 | 5.59 | 9.71 | 11.11 |
| Found | 61.82 | 5.72 | 9.26 | 10.51 |

IR spectrum (KBr): OH band at 3450 cm$^{-1}$, NH bands at 3260 and 3180 cm$^{-1}$, CH bands at 3080, 3000, 2950 and 2880 cm$^{-1}$, CO band at 1625 cm$^{-1}$, main bands at 1530, 1485, 1440, 1330, 1300, 1095, 830, 800, 710 and 690 cm$^{-1}$.

EXAMPLE 15

5,6-dihydro-6-(2-hydroxyphenethyl)-4-oxo-4H-pyrrolo[1,2-a]thieno[3,2-f][1,4]diazepine This compound was prepared from 5,6-dihydro-4-oxo-6-phenacyl-4H-pyrrolo[1,2-a]thieno[3,2-f][1,4]-diazepine (Tetrahedron Letters, 1979, No. 7, pp. 643–644) according to the process described in Example 12.

Yield: 79%.

Melting point: 190° C. (Ethyl ether), white crystals.

| Elemental analysis: | | | | |
|---|---|---|---|---|
| | C % | H % | N % | S % |
| Theory | 66.65 | 4.97 | 8.64 | 9.88 |
| Found | 66.56 | 4.89 | 8.52 | 9.68 |

IR spectrum (KBr): OH band at 3450 cm$^{-1}$, NH bands at 3250 and 3180 cm$^{-1}$, CH bands at 3030, 2955 and 2900 cm$^{-1}$, CO band at 1635 cm$^{-1}$, main bands at 1485, 1440, 1335, 1060 and 710 cm$^{-1}$.

EXAMPLE 16

5,6-dihydro-6-[2-hydroxy-2-(4-methylphenyl)ethyl]-4-oxo-4H-pyrrolo[1,2-a]thieno[3,2-f][1,4]diazepine This compound was prepared from the compound described in Example 4 and according to the process described in Example 12.
Yield: 71%.
Melting point: 182° C. (Ethyl ether), white crystals.

| Elemental analysis: | | | | |
|---|---|---|---|---|
| | C % | H % | N % | S % |
| Theory | 67.43 | 5.36 | 8.27 | 9.47 |
| Found | 67.30 | 5.44 | 8.16 | 9.33 |

IR spectrum (KBr): OH band at 3420 cm$^{-1}$, NH bands at 3250 and 3170 cm$^{-1}$, CH bands at 3100, 3020, 2950 and 2920 cm$^{-1}$, CO band at 1635 cm$^{-1}$, main bands at 1490, 1440, 1335, 1095, 1060, 830, 735 and 705 cm$^{-1}$.

EXAMPLE 17

5,6-dihydro-6-(2-hydroxy-3-methyl-1-butyl)-4-oxo-4H-pyrrolo[1,2-a]thieno[3,2-f][1,4]diazepine This compound was prepared from 5,6-dihydro-2-oxo-3-methyl-1-butyl)-4-oxo-4H-pyrrolo[1,2-a]thieno[3,2-f][1,4]diazepine according to the process described in Example 12.
Yield: 83%.
Melting point: 194° C. (Acetone), beige crystals.

| Elemental analysis: | | | | |
|---|---|---|---|---|
| | C % | H % | N % | S % |
| Theory | 62.04 | 6.24 | 9.64 | 11.04 |
| Found | 62.00 | 6.17 | 9.64 | 10.97 |

IR spectrum (KBr): OH band at 3460 cm$^{-1}$, NH bands at 3250 and 3170 cm$^{-1}$, CH bands at 3020, 2950, 2930 and 2870 cm$^{-1}$, CO band at 1625 cm$^{-1}$, main bands at 1530, 1490, 1445, 1330, 1100, 1055 and 710 cm$^{-1}$.

EXAMPLE 18

5,6-dihydro-6-[2-hydroxy-2-(2,5-dimethoxyphenyl)ethyl]-4-oxo-4H-pyrrolo[1,2-a]thieno[3,2-f][1,4]diazepine This compound was prepared from the compound of Example 6 according to the process described in Example 12.
Yield: 65%.
Melting point: 193° C. (Ethyl ether), white crystals.

| Elemental analysis: | | | | |
|---|---|---|---|---|
| | C % | H % | N % | S % |
| Theory | 62.48 | 5.24 | 7.28 | 8.33 |
| Found | 61.53 | 5.25 | 7.37 | 8.55 |

IR spectrum (KBr): OH band at 3420 cm$^{-1}$, NH bands at 3260 and 3180 cm$^{-1}$, CH bands at 3080, 3000, 2960, 2900 and 2820 cm$^{-1}$, CO band at 1625 cm$^{-}$, main bands at 1530, 1490, 1440, 1330, 1275, 1215, 1100, 1025, 800, 790 and 720 cm$^{-1}$.

EXAMPLE 19

4,6-dioxo-8-methyl-4,8,9,10-tetrahydro[1,3]oxazino[4,3-c]pyrrolo[1,2-a]thieno[3,2-f][1,4]diazepine 3 ml of a 20% solution of phosgene in toluene is added to a solution of 0.7 g of the compound obtained in Example 12 in 150 ml of toluene, and the reaction mixture is then heated to reflux for one hour. After cooling, the excess phosgene is removed by bubbling a stream of nitrogen through the reaction medium. The toluene is then removed under vacuum and the residue ground in 200 ml of water. The precipitate is drained, washed with water, dried and recrystallized.

EXAMPLE 20

4,6-dioxo-8-propyl-4,8,9,10-tetrahydro[1,3]oxazino[4,3-c]pyrrolo[1,2-a]thieno[3,2-f][1,4]diazepine This compound was obtained from the compound of Example 13 and according to the process described in the previous example.
Yield: 89%.
Melting point: 162° C. (Ethyl ether), white crystals.
IR spectrum (KBr): CH bands at 3020, 2960, and 2880 cm$^{-1}$, C=O bands at 1745 and 1665 cm$^{-1}$, main bands at 1385, 1280, 1195, 1160, 840 and 700 cm$^{-1}$.

EXAMPLE 21

4,6-dioxo-8-(4-methylphenyl)-4,8,9,10-tetrahydro[1,3]oxazino[4,3-c]pyrrolo[1,2-a]thieno[3,2-f][1,4]diazepine This compound was obtained from the compound of Example 16 and according to the process described above.
Yield: 78%.
Melting point: 240° C. (Ethyl ether), white crystals.

| Elemental analysis: | | | | |
|---|---|---|---|---|
| | C % | H % | N % | S % |
| Theory | 65.89 | 4.39 | 7.68 | 8.78 |
| Found | 65.72 | 4.33 | 7.61 | 8.72 |

IR spectrum (KBr): CH bands at 3030 and 2920 cm$^{-1}$, C=O bands at 1700 and 1625 cm$^{-1}$, main bands at 1490, 1440, 1330 and 715 cm$^{-1}$.

EXAMPLE 22

5,6-dihydro-6-(2-hydroxyimino-1-propyl)-4-oxo-4H-pyrrolo[1,2-a]thieno[3,2-f][1,4]diazepine A solution of 4.2 g of hydroxylamine hydrochloride and 4.92 g of sodium acetate in 20 ml of water is added to a solution of 4 g of 6-acetonyl-5,6-dihydro-4-oxo-4H-pyrrolo[1,2-a]thieno[3,2-f][1,4]diazepine in 500 ml of ethanol.

After the reaction medium has been heated to reflux for one hour, the ethanol is removed under vacuum. The residual solid is ground with 300 ml of water, drained, washed with water, dried and recrystallized.
Yield: 85%.
Melting point: 178° C. (Ethanol), white powder.

| Elemental analysis: | | | | |
|---|---|---|---|---|
| | C % | H % | N % | S % |
| Theory | 58.11 | 5.22 | 14.52 | 11.08 |
| Found | 57.99 | 5.16 | 14.47 | 11.10 |

IR spectrum (KBr): OH band at 3280 cm$^{-1}$, NH band at 3200 cm$^{-1}$, CH bands at 3100 and 2860 cm$^{-1}$, CO band at 1625 cm$^{-1}$, main bands at 1540, 1495, 1440, 1325, 1090, 930, 890 and 715 cm$^{-1}$.

EXAMPLE 23

5,6-dihydro-6-(2-hydroxyimino-3-methylbutyl)-4-oxo-4H-pyrrolo[1,2-a]thiene[3,2-f][1,4]diazepine A solution of 2.80 g of hydroxylamine hydrochloride and 3.3 g of sodium acetate in 15 ml of water is added to a solution of 3 g of 5,6-dihydro-6-(3-methyl-2-oxo-1-butyl)-4-oxo-4H-pyrrolo[1,2-a]thieno[3,2-f][1,4]diazepine in 300 ml of ethanol.

The reaction mixture is heated to reflux for one hour and the ethanol is then removed under vacuum. The residual solid is ground in 250 ml of water, drained, washed with water, dried and recrystallized.
Yield: 92%.
Melting point: 188° C. (Isopropanol), white crystals.

| Elemental analysis: | | | | |
|---|---|---|---|---|
| | C % | H % | N % | S % |
| Theory | 59.38 | 5.64 | 13.85 | 10.56 |
| Found | 59.46 | 5.69 | 13.78 | 10.46 |

IR spectrum (KBr): OH band at 3270-3130 cm$^{-1}$, NH band CH bands at 3100, 2960 and 2870 cm$^{-1}$, CO band at 1635 cm$^{-1}$, main bands at 1535, 1490, 1440, 1325, 1145, 1100, 950, 900, 785, 730 and 715 cm$^{-1}$.

EXAMPLE 24

5,6-dihydro-6-(2-cyclopropyl-2-hydroxyimino-1-ethyl)-4-oxo-4H-pyrrolo[1,2-a]thieno[3,2-f][1,4]diazepine A solution of 4.9 g of hydroxylamine hydrochloride and 5.8 g of sodium acetate in 20 ml of water is added to a solution of 5 g of the compound of Example 2 in 500 ml of ethanol.

After the mixture has been heated to reflux for one hour, the ethanol is removed under vacuum. The residual solid is ground with 300 ml of water and the precipitate formed is drained, washed with water, dried and recrystallized.
Yield: 87%.
Melting point: 210° C. (Ethyl ether), white crystals.

| Elemental analysis: | | | | |
|---|---|---|---|---|
| | C % | H % | N % | S % |
| Theory | 59.78 | 5.01 | 13.94 | 10.63 |
| Found | 59.91 | 5.03 | 14.08 | 10.46 |

IR spectrum (KBr): OH band at 3280-3150 cm$^{-1}$, NH band CH bands at 3100, 3000 and 2970 cm$^{-1}$, CO band at 1630 cm$^{-1}$, main bands at 1580, 1485, 1440, 1325, 1185, 1100, 935, 720 and 710 cm$^{-1}$.

EXAMPLE 25

5,6-dihydro-6-(2-hydroxyimino-1-pentyl)-4-oxo-4H-pyrrolo[1,2-a]thieno[3,2-f][1,4]diazepine This compound was prepared according to the process described above, starting with the compound of Example 1.
Yield: 82%.
Melting point: 110° C. (Ethyl ether).

| Elemental analysis: | | | | |
|---|---|---|---|---|
| | C % | H % | N % | S % |
| Theory | 59.39 | 5.65 | 13.85 | 10.57 |
| Found | 59.28 | 5.77 | 13.70 | 10.59 |

IR spectrum (KBr): OH band at 3280-3100 cm$^{-1}$, NH band CH bands at 3100, 2960, 2930 and 2880 cm$^{-1}$, CO band at 1640 cm$^{-1}$, main bands at 1540, 1490, 1440, 1325, 1090, 955, 780 and 710 cm$^{-1}$.

EXAMPLE 26

5,6-dihydro-6-(2-hydroxyiminophenethyl)-4-oxo-4H-pyrrolo[1,2-a]thieno[3,2-f][1,4]diazepine This compound was prepared from 5,6-dihydro-6-(2-oxophenethyl)-4-oxo-4H-pyrrolo[1,2-a]thieno[3,2-f][1,4]diazepine according to the process described above.
Yield: 82%.
Melting point: 228° C. (Ethyl ether), white crystals.

| Elemental analysis: | | | |
|---|---|---|---|
| | C % | H % | N % |
| Theory | 64.08 | 4.48 | 12.45 |
| Found | 63.93 | 4.60 | 12.32 |

IR spectrum (KBr): OH band at 3300 cm$^{-1}$, NH band CH bands at 3100, 3000 and 2830 cm$^{-1}$, CO band at 1630 cm$^{-1}$, main bands at 1495, 1450, 1325, 1150, 960, 770, 720 and 695 cm$^{-1}$.

EXAMPLE 27

5,6-dihydro-6-[2-hydroxyimino-2-(4-methylphenyl)-2-ethyl]-4-oxo-4H-pyrrolo[1,2-a]thieno[3,2-f][1,4]diazepine This compound was prepared from the compound of Example 4 according to the process described in Example 22.
Yield: 74%.
Melting point: 190° C. (Ethyl ether), white crystals.

| Elemental analysis: | | | | |
|---|---|---|---|---|
| | C % | H % | N % | S % |
| Theory | 64.95 | 4.84 | 11.96 | 9.12 |
| Found | 65.61 | 5.12 | 11.68 | 8.81 |

IR spectrum (KBr): OH band at 3300-3140 cm$^{-1}$, NH band CH bands at 3100, 2970 and 2850 cm$^{-1}$, CO band at 1625 cm$^{-1}$, main bands at 1535, 1490, 1445, 1325, 1185, 960, 820 and 720 cm$^{-1}$.

EXAMPLE 28

6-(2-cyclopropyl-2-methoxyimino-1-ethyl)-5,6-dihydro-4-oxo-4H-pyrrolo[1,2-a]thieno[3,2-f][1,4]diazepine A solution of 1 g of methoxylamine hydrochloride and 1.15 g of sodium acetate in 10 ml of water is added to a solution of 1 g of the compound of Example 2 in 150 ml of ethanol.

After the reaction mixture has been heated to reflux for one hour, the ethanol is removed under vacuum. After cooling, the residual solid is ground in 150 ml of water, drained, dried and recrystallized.

Yield: 82%.

Melting point: 152° C. (Ethyl ether), beige crystals.

|  | Elemental analysis: | | | |
|---|---|---|---|---|
|  | C % | H % | N % | S % |
| Theory | 60.93 | 5.43 | 13.32 | 10.16 |
| Found | 61.33 | 5.40 | 12.50 | 10.48 |

IR spectrum (KBr): NH bands at 3270 and 3190 cm$^{-1}$, CH bands at 3100, 2960 and 2930 cm$^{-1}$, CO band at 1645 cm$^{-1}$, main bands at 1535, 1490, 1435, 1330, 1100, 1005 and 715 cm$^{-1}$.

EXAMPLE 29

5,6-dihydro-6-(2-methoxyimino-1-propyl)-4-oxo-4H-pyrrolo[1,2-a]thieno[3,2-f][1,4]diazepine This compound was obtained according to the process described in Example 22, but replacing hydroxylamine hydrochloride by methoxylamine hydrochloride.

Yield: 93%.

Melting point: 138° C. (Ethyl ether), white flocculent product.

|  | Elemental analysis: | | | |
|---|---|---|---|---|
|  | C % | H % | N % | S % |
| Theory | 58.11 | 5.22 | 14.52 | 11.08 |
| Found | 57.99 | 5.16 | 14.47 | 11.10 |

IR spectrum (KBr): NH band at 3300 cm$^{-1}$, CH bands at 3100, 2950, 2930, 2890 and 2815 cm$^{-1}$, CO band at 1630 cm$^{-1}$, main bands at 1530, 1480, 1425, 1320, 1180, 1145, 1040, 710 and 690 cm$^{-1}$.

EXAMPLE 30

6-hydroxy-4-methoxy-6H-pyrrolo[1,2-a]thieno[3,2-f][1,4]diazepine

A suspension of 10 g (0.049 mole) of 3-cyano-2-(2-formyl-1-pyrrolyl)thiophene in 100 ml of 6N sodium hydroxide and 250 ml of methanol is heated slowly to 40° C. for one hour until dissolution is complete. The methanol is then removed under vacuum and the liquid residue is poured into 500 ml of water. The precipitate formed is Yield: 77%.

Melting point: 200° C. (Acetone), white crystals.

|  | Elemental analysis: | | | |
|---|---|---|---|---|
|  | C % | H % | N % | S % |
| Theory | 56.39 | 4.30 | 11.95 | 13.68 |
| Found | 56.39 | 4.39 | 12.00 | 13.83 |

IR spectrum (KBr): OH band at 3380 cm$^{-1}$, CH bands at 3100, 2980 and 2940 cm$^{-1}$, C=N band at 1640 cm$^{-1}$, main bands at 1540, 1480, 1330, 1260, 1100, 700 and 690 cm$^{-1}$.

EXAMPLE 31

4-ethoxy-6-hydroxy-6H-pyrrolo[1,2-a]thieno[3,2-f][1,4]diazepine

This compound was obtained as described in Example 30, but replacing methanol by ethanol.

Yield: 67%.

Melting point: 140° C. (Ethyl ether), white crystals.

|  | Elemental analysis: | | | |
|---|---|---|---|---|
|  | C % | H % | N % | S % |
| Theory | 58.04 | 4.87 | 11.28 | 12.91 |
| Found | 58.46 | 5.16 | 10.92 | 12.53 |

IR spectrum (KBr): OH band at 3400 cm$^{-1}$, CH bands at 3080, 2960, 2920 and 2850 cm$^{-1}$, C=N band at 1620 cm$^{-1}$, main bands at 1545, 1470, 1325, 1270, 1100, 785 and 700 cm$^{-1}$.

EXAMPLE 32

6-hydroxy-4-propoxy-6H-pyrrolo[1,2-a]thieno[3,2-f][1,4]diazepine

This compound was obtained as described in Example 30, but replacing methanol by 1-propanol.

Yield: 62%.

Melting point: 120° C. (Ethyl ether), white crystals.

|  | Elemental analysis: | | | |
|---|---|---|---|---|
|  | C % | H % | N % | S % |
| Theory | 59.52 | 5.38 | 10.68 | 12.22 |
| Found | 59.50 | 5.30 | 10.72 | 12.21 |

IR spectrum (KBr): OH bands between 3400 and 3300 cm$^{-1}$, CH bands at 3100 and 2960 cm$^{-1}$, C=N band at 1630 cm$^{-1}$, main bands at 1540, 1480, 1335, 1260, 1100, 1005 and 690 cm$^{-1}$.

EXAMPLE 33

4-allyloxy-6-hydroxy-6H-pyrrolo[1,2-a]thieno[3,2-f][1,4]diazepine

This compound was prepared as described in Example 30, but using allyl alcohol as an alcohol.

Yield: 64%.

Melting point: 122° C. (Ethyl ether), white flocculent product.

|  | Elemental analysis: | | |
|---|---|---|---|
|  | C % | H % | S % |
| Theory | 59.98 | 4.65 | 12.32 |
| Found | 60.15 | 4.68 | 12.20 |

IR spectrum (KBr): OH band at 3360 cm$^{-1}$, CH bands at 3100, 3000, 2920 and 2860 cm$^{-1}$, C=N band at 1630 cm$^{-1}$, main bands at 1535, 1480, 1320, 1245, 1085, 980 and 675 cm$^{-1}$.

EXAMPLE 34

4-methoxy-6-oxo-6H-pyrrolo[1,2-a]thieno[3,2-f][1,4]diazepine

A solution of 10 g of the compound of Example 30 and 20 g of potassium permanganate in 500 ml of acetone is stirred at room temperature for 4 hours. The precipitated manganese oxides are filtered off, the acetone is removed under vacuum and the residue is recrystallized.

Yield: 50%.

Melting point: 154° C. (Ethyl ether), white needles.

| Elemental analysis: | | | | |
|---|---|---|---|---|
| | C % | H % | N % | S % |
| Theory | 56.89 | 3.47 | 12.06 | 13.80 |
| Found | 57.01 | 3.31 | 12.02 | 13.61 |

IR spectrum (KBr): CH bands at 3110, 3075 and 2950 cm$^{-1}$, C=O band at 1630 cm$^{-1}$, C=N band at 1600 cm$^{-1}$, main bands at 1550, 1545, 1445, 1355, 1330, 1280, 1190, 1020, 770 and 725 cm$^{-1}$.

EXAMPLE 35

4-ethoxy-6-oxo-6H-pyrrolo[1,2-a]thieno[3,2-f][1,4]diazepine

This compound was prepared from the compound of Example 31 according to the process described above.

Yield: 55%.

Melting point: 188° C. (Ethyl ether), white needles.

| Elemental analysis: | | | | |
|---|---|---|---|---|
| | C % | H % | N % | S % |
| Theory | 58.52 | 4.09 | 11.37 | 13.02 |
| Found | 58.48 | 4.04 | 11.29 | 12.93 |

IR spectrum (KBr): CH bands at 3120, 3070 and 2990 cm$^{-1}$, C=O band at 1635 cm$^{-1}$, C=N band at 1590 cm$^{-1}$, main bands at 1550, 1540, 1350, 1325, 1265, 1180, 1030, 765 and 720 cm$^{-1}$.

EXAMPLE 36

6-oxo-4-propoxy-6H-pyrrolo[1,2-a]thieno[3,2-f][1,4]diazepine

This compound was prepared from the compound described in Example 32 according to the process described in Example 34.

Yield: 55%.

Melting point: 130° C. (Ethyl ether), white needles.

| Elemental analysis: | | | | |
|---|---|---|---|---|
| | C % | H % | N % | S % |
| Theory | 59.98 | 4.65 | 10.76 | 12.32 |
| Found | 59.84 | 4.55 | 10.75 | 12.45 |

IR spectrum (KBr): CH bands at 3310, 3075, 2985, 2940 and 2880 cm$^{-1}$, C=O band at 1640 cm$^{-1}$, C=N band at 1600 cm$^{-1}$, main bands at 1555, 1540, 1440, 1320, 1260, 1170, 980, 730 and 705 cm$^{-1}$.

EXAMPLE 37

5,6-dihydro-4-methoxy-6-oxo-4H-pyrrolo[1,2-a]thieno[3,2-f][1,4]diazepine 1.30 g of sodium borohydride are added in small portions to a solution of 2 g of the compound of Example 34 in 200 ml of methanol, and the reaction mixture is then stirred at room temperature for 3 hours. The methanol is then removed under vacuum and the solid residue is ground in 200 ml of water, drained, washed with water, dried and recrystallized.

Yield: 74%.

Melting point: 205° C. (Ethyl ether), white crystals.

| Elemental analysis: | | | | |
|---|---|---|---|---|
| | C % | H % | N % | S % |
| Theory | 56.40 | 4.30 | 11.96 | 13.68 |
| Found | 56.39 | 4.21 | 11.99 | 13.52 |

IR spectrum (KBr): NH band at 3260 cm$^{-1}$, CH bands at 3100, 3000, 2950 and 2840 cm$^{-1}$, CO band at 1650 cm$^{-1}$, main bands at 1590, 1470, 1400, 1320, 1075, 770 and 715 cm$^{-1}$.

EXAMPLE 38

5,6-dihydro-4-ethoxy-4H-pyrrolo[1,2-a]thieno[3,2-f][1,4]diazepine

This compound was prepared from the compound of Example 35 according to the process described above.

Yield: 70%.

Melting point: 170° C. (Ethyl ether), white crystals.

| Elemental analysis: | | | | |
|---|---|---|---|---|
| | C % | H % | N % | S % |
| Theory | 58.05 | 4.87 | 11.28 | 12.91 |
| Found | 57.88 | 4.74 | 11.35 | 12.77 |

IR spectrum (KBr): NH band at 3260 cm$^{-1}$, CH bands at 3120, 2695 and 2880 cm$^{-1}$, CO band at 1640 cm$^{-1}$, main bands at 1590, 1540, 1460, 1390, 1060, 755 and 700 cm$^{-1}$.

EXAMPLE 39

5,6-dihydro-6-oxo-4-propoxy-4H-pyrrolo[1,2-a]thieno[1,4]diazepine

This compound was prepared from the compound of Example 36 according to the process described in Example 37.

Yield: 54%.

Melting point: 160° C. (Ethyl ether), white crystals.

| Elemental analysis: | | | | |
|---|---|---|---|---|
| | C % | H % | N % | S % |
| Theory | 59.52 | 5.38 | 10.68 | 12.22 |
| Found | 59.27 | 5.25 | 10.67 | 12.06 |

IR spectrum (KBr): NH band at 3295 cm$^{-1}$, CH bands at 3105, 2930 and 2880 cm$^{-1}$, CO band at 1650 cm$^{-1}$, main bands at 1595, 1545, 1460, 1390, 1305, 1075, 1030 and 760 cm$^{-1}$.

EXAMPLE 40

5,6-dihydro-6-hydroxy-4-oxo-4H-pyrrolo[1,2-a]thieno-[3,2-f]1,4]diazepine 0.5 ml of triethylamine is added to a suspension of 2 g of 3-carbamoyl-2-(2-formyl-1-pyrrolyl)thiophene in 60 ml of water, and the reaction mixture is then stirred for 12 hours at room temperature. The product passes gradually into solution and then reprecipitates. The precipitate obtained is drained, washed with water, dried and recrystallized.

Yield: 68%.

Melting point: 166° C. (Water), beige needles.

| | Elemental analysis: | | | |
|---|---|---|---|---|
| | C % | H % | N % | S % |
| Theory | 54.53 | 3.66 | 12.71 | 14.56 |
| Found | 54.36 | 3.69 | 12.58 | 14.39 |

IR spectrum (KBr): OH band at 3340 cm$^{-1}$, NH band at 3220 cm$^{-1}$, CH bands at 3120 and 3110 cm$^{-1}$, C=O band at 1610 cm$^{-1}$, main bands at 1500, 1450, 1320, 1205, 1005, 830 and 720 cm$^{-1}$.

Proton NMR spectrum (solvent DMSO-d$_6$):

| $H_2$ ppm | $H_3$ ppm | $H_7$ ppm | $H_8$ ppm | $H_9$ ppm | NH ppm | $H_6$ ppm | Other protons |
|---|---|---|---|---|---|---|---|
| 7.20 | 7.20 | 6.25 | 6.25 | 7.18 | 8.94 | 5.62 | OH: 6.33 |

EXAMPLE 41

5.6-dihydro-6-methylamino-4-oxo-4H-pyrrolo[1,2-a]thieno[3,2-f]1,4]diazepine

Process A 10 ml of a 35% aqueous solution of methylamine are added to a suspension of 1.5 g of the compound obtained in Example 40 in 50 ml of water. The precipitate formed at the end of the reaction is drained, washed with water, dried and recrystallized.

Yield: 88%.

Process B 8 ml of a 35% aqueous solution of methylamine in 50 ml of water are added to a solution of 1 g of 3-carbamoyl-2-(2-formyl-1-pyrrolyl)thiophene in 50 ml of acetonitrile. The reaction mixture is heated to reflux for approximately 3 hours. The acetonitrile is then removed under vacuum and the residue recrystallized in ethyl ether.

Yield: 84%.

Melting point: 168° C. (Ethyl ether), white crystals.

| | Elemental analysis: | | | |
|---|---|---|---|---|
| | C % | H % | N % | S % |
| Theory | 56.63 | 4.75 | 18.01 | 13.74 |
| Found | 56.55 | 4.73 | 17.88 | 13.69 |

IR spectrum (KBr): NH bands at 3320, 3250 and 3170 cm$^{-1}$, CH bands at 3100, 3040, 2980, 2930 and 2860 cm$^{-1}$, C=O band at 1635 cm$^{-1}$, main bands at 1535, 1490, 1435, 1330, 1315, 1120, 1090, 820, 750 and 705 cm$^{-1}$.

EXAMPLE 42

5,6-dihydro-6-ethylamino-4-oxo-4H-pyrrolo[1,2-a]thieno[3,2-f][1,4]diazepine

The procedure is as described in Example 41 (Process A or B), using an aqueous solution of ethylamine (70%) instead of an aqueous solution of methylamine.

Yield: (Process A)=89%, (Process B)=80%.

Melting point: 156° (Ethyl ether), white crystals.

| | Elemental analysis: | | | |
|---|---|---|---|---|
| | C % | H % | N % | S % |
| Theory | 58.28 | 5.30 | 16.99 | 12.96 |
| Found | 58.26 | 5.25 | 16.99 | 12.87 |

IR spectrum (KBr): NH bands at 3300, 3240 and 3140 cm$^{-1}$, CH bands at 3020, 2940 and 2850 cm$^{-1}$, C=O bands at 1630 cm$^{-1}$, main bands at 1525, 1475, 1450, 1420, 1315, 1115, 1070, 770, 705, 690 and 660 cm$^{-1}$.

EXAMPLE 43

5,6-dihydro-4-oxo-6-propylamino-4H-pyrrolo[1,2-a]thieno[3,2-f][1,4]diazepine

To obtain this compound, the procedure is as in Example 41 (Process A), using propylamine instead of methylamine.

Melting point: 130° (Ethyl ether), white crystals.

| | Elemental analysis: | | | |
|---|---|---|---|---|
| | C % | H % | N % | S % |
| Theory | 59.75 | 5.78 | 16.08 | 12.87 |
| Found | 59.63 | 5.82 | 15.95 | 12.13 |

IR spectrum (KBr): NH bands at 3340, 3260 and 3170 cm$^{-1}$, CH bands at 3100, 3040, 2960, 2930 and 2860 cm$^{-1}$, C=O band at 1635 cm$^{-1}$, main bands at 1540, 1495, 1435, 1330, 1095 and 740 cm$^{-1}$.

EXAMPLE 44

5,6-dihydro-6-isopropylamino-4-oxo-4H-pyrrolo[1,2-a]thieno[3,2-f][1,4]diazepine

The procedure is as in the previous example, using isopropylamine instead of propylamine.

Yield: 76%.

Melting point: 152° C. (Ethyl ether), yellow crystals.

| | Elemental analysis: | | | |
|---|---|---|---|---|
| | C % | H % | N % | S % |
| Theory | 59.75 | 5.78 | 16.08 | 12.27 |

-continued

| | Elemental analysis: | | | |
|---|---|---|---|---|
| | C % | H % | N % | S % |
| Found | 59.67 | 5.88 | 16.18 | 12.12 |

IR spectrum (KBr): NH bands at 3330, 3250 and 3170 cm$^{-1}$, CH bands at 3040, 2970 and 2870 cm$^{-1}$, CO band at 1625 cm$^{-1}$, main bands at 1485, 1430, 1320, 1180, 1090, 815, 790, 750, 690 and 670 cm$^{-1}$.

EXAMPLE 45

5,6-dihydro-6-dimethylamino-4-oxo-4H-pyrrolo[1,2-a]thieno[3,2-f][1,4]diazepine

The procedure is as in Example 43, using a 40% aqueous solution of dimethylamine.
Yield: 63%.
Melting point: 180° C. (Ethyl ether), white crystals.

| | Elemental analysis: | | | |
|---|---|---|---|---|
| | C % | H % | N % | S % |
| Theory | 58.28 | 5.30 | 16.99 | 12.96 |
| Found | 58.12 | 5.22 | 16.91 | 13.09 |

IR spectrum (KBr): NH bands at 3280 and 3180 cm$^{-1}$, CH bands at 3060, 2950, 2940, 2820 and 2780 cm$^{-1}$, CO band at 1650 cm$^{-1}$, main bands at 1540, 1490, 1440, 1325, 1300, 1215, 995, 810, 800, 715 and 695 cm$^{-1}$.

EXAMPLE 46

5,6-dihydro-6-diethylamino-4-oxo-4H-pyrrolo[1,2-a]thieno[3,2-f][1,4]diazepine

The procedure is as in Example 45, starting with 1 g of the compound of Example 40 and 3 ml of diethylamine in 50 ml of water.
Yield: 65%.
Melting point: 137° C. (Ethyl ether), white crystals.

| | Elemental analysis: | | | |
|---|---|---|---|---|
| | C % | H % | N % | S % |
| Theory | 61.06 | 6.22 | 15.26 | 11.64 |
| Found | 60.99 | 6.21 | 15.31 | 11.86 |

IR spectrum (KBr): NH bands at 3275 and 3185 cm$^{-1}$, CH bands at 3050, 2960, 2930 and 2820 cm$^{-1}$, CO band at 1645 cm$^{-1}$, main bands at 1545, 1500, 1445, 1325, 1215, 1090, 1025 and 705 cm$^{-1}$.

EXAMPLE 47

5,6-dihydro-4-oxo-6-(1-pyrrolidinyl)-4H-pyrrolo[1,2-a]thieno[3,2-f][1,4]diazepine The procedure is as in Example 45, using 8 g of the compound of Example 40 and 4 ml of pyrrolidine in ml of water.
Yield: 89%.
Melting point: 176° C. (Ethyl ether), white crystals.

| | Elemental analysis: | | | |
|---|---|---|---|---|
| | C % | H % | N % | S % |
| Theory | 61.52 | 5.53 | 15.37 | 11.73 |
| Found | 61.65 | 5.58 | 15.46 | 11.80 |

IR spectrum (KBr): NH bands at 3280 and 3180 cm$^{-1}$, CH bands at 3060, 2950, 2930 and 2790 cm$^{-1}$, CO band at 1645 cm$^{-1}$, main bands at 1540, 1500, 1445, 1325, 1310, 1215, 1125, 895, 825, 805, 720 and 705 cm$^{-1}$.

EXAMPLE 48

5,6-dihydro-4-oxo-6-piperidino-4H-pyrrolo[1,2-a]thieno[3,2-f][1,4]diazepine

The procedure is as in Example 45, using 1.5 g of the compound of Example 40 and 3 ml of piperidine in ml of water.
Yield: 86%.
Melting point: 150° C. (Ethyl ether), white crystals.

| | Elemental analysis: | | | |
|---|---|---|---|---|
| | C % | H % | N % | S % |
| Theory | 62.69 | 5.96 | 14.62 | 11.16 |
| Found | 61.43 | 5.87 | 14.50 | 10.90 |

IR spectrum (KBr): NH bands at 3270 and 3190 cm$^{-1}$, CH bands at 3060, 2940, 2860, 2800 and 2760 cm$^{-1}$, CO band at 1650 cm$^{-1}$, main bands at 1540, 1495, 1445, 1325, 1310, 1230, 1100, 980, 880 and 710 cm$^{-1}$.

EXAMPLE 49

5,6-dihydro-4-oxo-6-(4-morpholinyl)-4H-pyrrolo[1,2-a]thieno[3,2-][1,4]diazepine

The procedure is as in Example 48, using 3 ml of morpholine.
Yield: 65%.
Melting point: 180° C. (Ethyl ether), white crystals.

| | Elemental analysis: | | | |
|---|---|---|---|---|
| | C % | H % | N % | S % |
| Theory | 58.11 | 5.22 | 14.52 | 11.08 |
| Found | 58.13 | 5.23 | 14.64 | 10.94 |

IR spectrum (KBr): NH bands at 3280 and 3200 cm$^{-1}$, CH bands at 3110, 3060, 2960, 2910 and 2810 cm$^{-1}$, CO band at 1645 cm$^{-1}$, main bands at 1545, 1495, 1440, 1330, 1110, 1000, 870, 790 and 700 cm$^{-1}$.

EXAMPLE 50

5,6-dihydro-4-oxo-6-(4-ethoxycarbonylpiperazino)-4H-pyrrolo[1,2-a]thieno[3,2-f][1,4]diazepine The procedure is as for Example 45, starting with 2 g of the compound of Example 40 and 5 ml of N-ethoxycarbonylpiperazine in 100 ml of water.
Yield: 80%.
Melting point: 200° C. (Ethyl ether), white crystals.

| | Elemental analysis: | | | |
|---|---|---|---|---|
| | C % | H % | N % | S % |
| Theory | 56.65 | 5.59 | 15.54 | 8.89 |
| Found | 56.23 | 5.41 | 15.34 | 8.45 |

IR spectrum (KBr): NH bands at 3280 and 3180 cm$^{-1}$, CH bands at 3050, 2940, 2810 and 2775 cm$^{-1}$, CO bands at 1690 and 1650 cm$^{-1}$, main bands at 1435, 1250, 1230, 1120, 996 and 715 cm$^{-1}$.

EXAMPLE 51

5,6-dihydro-4-oxo-6-anilino-4H-pyrrolo[1,2-a]thieno[3,2-f][1,4]diazepine

A solution of 1 9 of the compound of Example 1 in 20 ml of dioxane is added in a sin9 1e portion to an emulsion of 5 ml of aniline in 10 cm³ of 1N sodium hydroxide, and the reaction medium is then stirred at room temperature for 6 hours.

300 ml of water are then poured into the emulsion obtained. The precipitate formed is drained, washed with water, dried and recrystallized.

Yield: 75%.

Melting point: 160° C. (Ethyl ether), white flocculent product.

| | Elemental analysis: | | | |
|---|---|---|---|---|
| | C % | H % | N % | S % |
| Theory | 65.07 | 4.44 | 14.23 | 10.85 |
| Found | 64.67 | 4.56 | 14.01 | 11.10 |

IR spectrum (KBr): NH bands at 3340, 3280 and 3190 cm$^{-1}$, CH bands at 3110 and 3060 cm$^{-1}$, CO band at 1645 cm$^{-1}$, main bands at 1605, 1500, 1330, 1310, 1260, 755 and 700 cm$^{-1}$.

EXAMPLE 52

5,6-dihydro-4-oxo-6-(N-benzylamino)-4H-pyrrolo-[1,2-a]thieno[3,2-f][1,4]diazepine The procedure is as for Example 45, starting with 2 g of the compound of Example 40 and 7.5 ml of benzylamine in 100 ml of water.

Yield: 70%.

Melting point: 148° C. (Ethyl ether), white flocculent product.

| | Elemental analysis: | | | |
|---|---|---|---|---|
| | C % | H % | N % | S % |
| Theory | 66.00 | 4.89 | 13.58 | 10.36 |
| Found | 65.84 | 4.91 | 13.44 | 10.55 |

IR spectrum (KBr): NH bands at 3340 and 3220 cm$^{-1}$, CH bands at 3090 and 2900 cm$^{-1}$, CO band at 1635 cm$^{-1}$, main bands at 1500, 1465, 1330, 1230, 740, 715 and 700 cm$^{-1}$.

EXAMPLE 53

5,6-dihydro-4-oxo-4H-pyrrolo[1,2-a]thieno[3,2-f][1,4]diazepine 0.62 g of sodium borohydride is added in small portions to a solution of 1.5 g of the compound obtained in Example 49 in 150 ml of methanol, and the reaction mixture is stirred at room temperature for 15 minutes and then heated to reflux for 30 min. The methanol is then removed under vacuum and the solid residue ground in 200 ml of water. The precipitate formed is drained, washed with water, dried and recrystallized.

Yield: 86%.

| | Elemental analysis: | | | |
|---|---|---|---|---|
| | C % | H % | N % | S % |
| Theory | 58.81 | 3.95 | 13.72 | 15.70 |
| Found | 59.02 | 3.87 | 13.78 | 15.65 |

IR spectrum (KBr): NH bands at 3280 and 3170 cm$^{-1}$, CH bands at 3090 and 2900 cm$^{-1}$, CO band at 1660 cm$^{-1}$, main bands at 1540, 1495, 1460, 1225, 1095, 910, 750, 680 and 620 cm$^{-1}$.

Proton nuclear magnetic resonance spectrum (solvent CDCl$_3$):

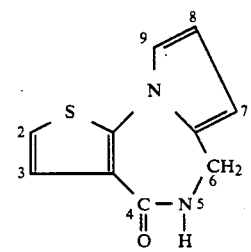

| H$_2$ ppm | H$_3$ ppm | H$_7$ ppm | H$_8$ ppm | H$_9$ ppm | NH ppm | CH$_2$ 6 |
|---|---|---|---|---|---|---|
| 7.39 | 6.93 | 6.13 | 6.29 | 6.96 | 6.60 | 4.29 |

EXAMPLE 54 ethyl (5,6-dihydro-4-oxo-4H-pyrrolo[1,2-a]thieno[3,2-f][1,4]diazepin-6-yl)cyanoacetate 2 ml of ethyl cyanoacetate and 0.5 ml of triethylamine are added to a solution of 1 g of the compound of Example 40 in 100 ml of acetonitrile. The reaction mixture is stirred at room temperature for 12 hours. The acetonitrile is then removed under vacuum. The oily residue is ground in 200 ml of water. The precipitate formed is drained, washed with water, dried and recrystallized.

Yield: 49%.

Melting point: 208° C. (Ethyl ether), yellow crystal.

| | Elemental analysis: | | | |
|---|---|---|---|---|
| | C % | H % | N % | S % |
| Theory | 57.13 | 4.16 | 13.33 | 10.17 |
| Found | 56.99 | 4.17 | 13.15 | 10.03 |

IR spectrum (KBr): NH bands at 3400 and 3220 cm$^{-1}$, CH bands at 3050 and 3300 cm$^{-1}$, C≡N band at 2270 cm$^{-1}$, CO bands at 1720 (ester) and 1685 (lactam) cm$^{-1}$, main bands at 1590, 1470, 1425, 1240, 1095, 760 and 710 cm$^{-1}$.

Proton nuclear magnetic resonance spectrum (solvent DMSO-d$_6$):

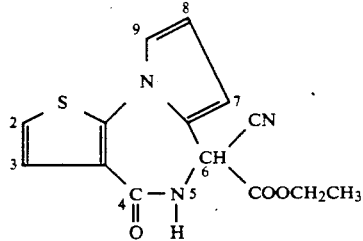

| H$_2$ ppm | H$_3$ ppm | H$_7$ ppm | H$_8$ ppm | H$_9$ ppm | NH ppm | H$_6$ ppm | Other protons |
|---|---|---|---|---|---|---|---|
| 7.76 | 7.50 | 7.43 | 7.61 | 7.67 | 7.61 | 6.64 | CH$_2$: 4.20 <br> CH$_3$: 1.22 |

EXAMPLE 55

5,6-dihydro-6-(1-methylethoxy)-4-oxo-4H-pyrrolo-[1,2-a]thieno[3,2-f][1,4]diazepine A solution of 1 g of 3-carbamoyl-2-(2-formyl-1-pyrrolyl)thiophene in 60 ml of isopropanol is heated to reflux for one hour. The isopropanol is then removed under vacuum and the residual solid recrystallized.

Yield: 93%.

Melting point: 165° C. (Isopropanol), white crystals.

| | Elemental analysis: | | | |
|---|---|---|---|---|
| | C % | H % | N % | S % |
| Theory | 59.52 | 5.37 | 10.67 | 12.22 |
| Found | 59.71 | 5.36 | 10.84 | 12.18 |

IR spectrum (KBr): NH bands at 3270 and 3180 cm$^{-1}$, CH bands at 3050, 2960 and 2880 cm$^{-1}$, C=O band at 1645 cm$^{-1}$, main bands at 1540, 1500, 1320, 1230, 1215, 1020, 730 and 705 cm$^{-1}$.

Process B

Same protocol as ior Process A, but 1 g of the compound described in Example 40 is used instead of 3-carbamoyl-2-(2-formyl-1-pyrrolyl)thiophene.

Yield: 93%.

EXAMPLE 56

6-benzyloxy-5,6-dihydro-4-oxo-4H-pyrrolo[1,2-a]thieno[3,2-f][1,4]diazepine 0.0050 mole of benzyl alcohol is added to a solution of 0.0045 mole of the compound of Example 40 in 100 ml of acetonitrile, and the reaction mixture is then heated to reflux for 90 min. The acetonitrile is then removed under vacuum. The residual oil which crystallizes on addition of petroleum ether is recrystallized.

Yield: 86%.

Melting point: 150° C. (Ethyl ether), white crystals.

| | Elemental analysis: | | | |
|---|---|---|---|---|
| | C % | H % | N % | S % |
| Theory | 65.79 | 4.55 | 10.33 | 9.02 |
| Found | 65.41 | 4.37 | 10.45 | 9.22 |

IR spectrum (KBr): NH bands at 3260 and 3190 cm$^{-1}$, CH bands at 3100, 3060, 2920 and 2860 cm$^{-1}$, C=O band at 1635 cm$^{-1}$, main bands at 1540, 1490, 1440, 1310, 1025, 920, 710 and 685 cm$^{-1}$.

EXAMPLE 57

5,6-dihydro-6-(N',N'-dimethylhydrazino)-4-oxo-4H-pyrrolo[1,2-a]thieno[3,2-f][1,4]diazepine 2 ml of dimethyl hydrazine are added to a suspension of 1 g of 3-carbamoyl-2-(2-formyl-1-pyrrolyl)thiophene in 300 ml of water. The reaction mixture is heated to 50° C. for 30 min and then stirred at room temperature for 12 hours. The orange solution obtained is extracted with twice 100 ml of ethyl ether. The organic phases are combined, washed with water, dried over sodium sulfate and taken down under vacuum. The residual oil which crystallizes on addition of petroleum ether is recrystallized.

Yield: 76%.

Melting point: 116° C. (Ethanol) pink crystals.

| | Elemental analysis: | | | |
|---|---|---|---|---|
| | C % | H % | N % | S % |
| Theory | 54.94 | 5.38 | 21.36 | 12.22 |
| Found | 54.11 | 5.10 | 20.61 | 12.05 |

IR spectrum (KBr): NH bands at 3280 and 3140 cm$^{-1}$, CH bands at 3000, 2950, 2860 and 2790 cm$^{-1}$, CO band at 1675 cm$^{-1}$, main bands at 1450, 1420, 1330, 1050, 860, 795 and 715 cm$^{-1}$.

EXAMPLE 58

5,6-dihydro-1-oxo-6-(N'-phenylhydrazino)-4H-pyrrolo[1,2-a]thieno[3,2-f][1,4]diazepine This compound was prepared according to the process described in Example 57, but using phenylhydrazine.

Yield: 71%.

Melting point: 158° C. (Ethyl ether), gray crystals.

| | Elemental analysis: | | | |
|---|---|---|---|---|
| | C % | H % | N % | S % |
| Theory | 61.92 | 4.55 | 18.05 | 10.33 |
| Found | 62.12 | 4.66 | 17.89 | 10.43 |

IR spectrum (KBr): NH bands at 3460, 3320, 3280 and 3150 cm$^{-1}$, CH bands at 3100 and 3040 cm$^{-1}$, CO band at 1660 cm$^{-1}$, main bands at 1580, 1490, 1460, 1280, 1255, 1125, 750, 715 and 690 cm$^{-1}$.

EXAMPLE 59

5,6-dihydro-6-[N'-(2,5-dinitrophenylhydrazino)]-4-oxo-4H-pyrrolo[1,2-a]thieno[3,2-f][1,4]diazepine This compound was prepared according to the process described in Example 57, but using 2,5-dinitrophenylhydrazine.

Yield: 65%.

Melting point: 238° C. (Ethyl ether/acetone), red crystals.

| | Elemental analysis: | | | |
|---|---|---|---|---|
| | C % | H % | N % | S % |
| Theory | 48.10 | 3.01 | 8.00 | 21.00 |
| Found | 47.92 | 2.98 | 8.02 | 20.79 |

IR spectrum (KBr): NH bands at 3270 and 3120 cm$^{-1}$, CH bands at 3110 and 3090 cm$^{-1}$, C=O band at 1650 cm$^{-1}$, main bands at 1615, 1500, 1420, 1340, 1320, 1135, 1090 and 715 cm$^{-1}$.

EXAMPLE 60

5,6-dihydro-6-(methoxycarbonylmethylthio)-4-oxo-4H-pyrrolo[1,2-a]thieno[3,2-f][1,4]diazepine A solution of 1 g of 3-carbamoyl-2-(2-formyl-1-pyrrolyl)thiophene in 100 ml of acetonitrile is treated with 0.43 ml (0.005 mole) of methyl thioglycolate, and the reaction mixture is stirred overnight at room temperature. The acetonitrile is then removed under vacuum. The residual oil which crystallizes on addition of petroleum ether is recrystallized.

Yield 72%.

Melting point: 158° C. (Ethyl ether), white crystals.

| Elemental analysis: | | | | |
|---|---|---|---|---|
| | C % | H % | N % | S % |
| Theory | 50.64 | 3.92 | 9.08 | 20.73 |
| Found | 50.50 | 3.83 | 9.02 | 20.95 |

IR spectrum (KBr): NH bands at 3360 and 3280 cm$^{-1}$, CH bands at 3050 and 2950 cm$^{-1}$, CO bands at 1730 (ester) and 1645 (lactam) cm$^{-1}$, main bands at 1535, 1495, 1440, 1310, 1240, 1165, 790, 735 and 705 cm$^{-1}$.

EXAMPLE 61

5,6-dihydro-6-phenylthio-4-oxo-4H-pyrrolo[1,2-a]thieno[3,2-f][1,4]diazepine

This compound was prepared according to the process described Example 60, but using thiophenol instead of methyl thioglycolate.

Yield: 78%.

Melting point: 142° C. (Ethyl ether), white crystals.

| Elemental analysis: | | | | |
|---|---|---|---|---|
| | C % | H % | N % | S % |
| Theory | 61.51 | 3.87 | 8.97 | 20.52 |
| Found | 60.65 | 3.82 | 9.13 | 20.69 |

IR spectrum (KBr): NH bands at 3370 and 3160 cm$^{-1}$, CH bands at 3120, 3010 and 2930 cm$^{-1}$, CO band at 1645 cm$^{-1}$, main bands at 1550, 1500, 1480, 1325, 1220, 1065, 775, 720 and 690 cm$^{-1}$.

EXAMPLE 62

3-(5,6-dihydro-4-oxo-4H-pyrrolo[1,2-a]thieno[3,2-f][1,4]diazepin-6-ylthio)propionic acid This compound was prepared according to the process described in Example 60, but using 3-mercaptopropionic acid instead of methyl thioglycolate.

Yield: 50%.

Melting point: 153° C. (Ethyl ether), white crystals.

| Elemental analysis: | | | | |
|---|---|---|---|---|
| | C % | H % | N % | S % |
| Theory | 50.64 | 3.92 | 9.08 | 20.79 |
| Found | 50.48 | 3.89 | 9.07 | 20.71 |

IR spectrum (KBr): OH band at 3450 cm$^{-1}$, NH bands at 3260 and 3200 cm$^{-1}$, CH bands at 3060 and 2940 cm$^{-1}$, C=O bands at 1700 (acid) and 1645 (lactam) cm$^{-1}$, main bands at 1550, 1500, 1430, 1245, 1190, 925 and 710 cm$^{-1}$.

EXAMPLE 63

3-(5,6-dihydro-4-oxo-4H-pyrrolo[1,2-a]thieno[1,4-]diazeoin-6-ylthio)propionamide 0.50 ml (0.0035 mole) of triethylamine is added in a single portion to a suspension, cooled beforehand to 0° C., of 1 g of the compound of Example 62 in 150 ml of ethyl ether, the reaction mixture is then stirred for 20 min at the same temperature, 0.30 ml of ethyl chloroformate are thereafter added dropwise and stirring is continued for 20 min at 0° C. The product gradually passes into solution and the appearance of a flocculent precipitate of triethylamine hydrochloride is observed. The latter is filtered off and a stream of gaseous ammonia is passed into the ethereal solution, still maintained at 0° C., for 20 seconds. The white precipitate obtained is drained, washed with ethyl ether and recrystallized.

Yield: 25%.

| Elemental analysis: | | | | |
|---|---|---|---|---|
| | C % | H % | N % | S % |
| Theory | 50.80 | 4.26 | 13.67 | 20.86 |
| Found | 50225 | 4.67 | 14.03 | 21.66 |

IR spectrum (KBr): NH bands at 3460, 3340 and 3170 cm$^{-1}$, CH bands at 3040, 2960 and 2920 cm$^{-1}$, C=O band at 1660 cm$^{-1}$, main bands at 1490, 1430, 1410, 1425, 1090, 750 and 710 cm$^{-1}$.

EXAMPLE 64

5,6-dihydro-6-(2-benzoyloxypropyl)-4-oxo-4H-pyrrolo[1,2-a]thieno[3,2-f][1,4]diazepine 0.55 ml of benzoyl chloride is added to a solution of 0.7 g of 5,6-dihydro-6-(2-hydroxypropyl)-4-oxo-4H-pyrrolo[1,2-a]thieno[3,2-f][1,4]diazepine (compound of Example 12) in 10 ml of pyridine. The reaction medium is stirred for 24 hours at room temperature and the pyridine is then removed under vacuum.

The residue is taken up with 100 ml of water and the product extracted with 150 ml of ethyl ether.

The organic phase is washed with water, dried over magnesium sulfate and then concentrated.

The residual oil which crystallizes on addition of petroleum ether is recrystallized in ethyl ether.

Yield: 25%.

Melting point: 95° C. (Ethyl ether), white crystals.

| Elemental analysis | | | | |
|---|---|---|---|---|
| | C % | H % | N % | S % |
| Theory | 65.56 | 4.95 | 7.64 | 8.75 |
| Found | 66.01 | 4.72 | 6.22 | 8.92 |

IR spectrum (KBr): NH bands at 3260 and 3140 cm$^{-1}$, CH bands at 2980, 2960 and 2890 cm$^{-1}$, CO bands at 1730 and 1675 cm$^{-1}$, main bands at 1550, 1500, 1290, 1245, 1100 and 720 cm$^{-1}$.

EXAMPLE 65

5,6-dihydro-6-(2-hydrazono-1-pentyl)-4-oxo-4H-pyrrolo[1,2-a]thieno[3,2-f][1,4]diazepine 0.6 ml of hydrazine hydrate is added to a solution of 1 g of 5,6-dihydro-4-oxo-6-(2-oxo-1-pentyl)-4H-pyrrolo[1,2-a]thieno[3,2-f][1,4]diazepine (Example 1) in 250 ml of ethanol, and the reaction mixture is then heated to reflux for one hour. The ethanol is then removed under vacuum and the residual solid ground in 100 ml of water.

The precipitate formed is drained, washed, dried and recrystallized.

Yield: 76%.

Melting point: 158° C. (Ethyl ether), white crystals.

| Elemental analysis: | | | | |
|---|---|---|---|---|
| | C % | H % | S % | N % |
| Theory | 59.78 | 5.69 | 18.59 | 10.64 |
| Found | 59.45 | 5.88 | 18.21 | 10.31 |

IR spectrum (KBr): NH bands at 3410, 3370 and 3190 cm$^{-1}$, CH bands at 3050, 2970 and 2880 cm$^{-1}$, CO band at 1640 cm$^{-1}$, main bands at 1490, 1435, 1335, 1090 and 715 cm$^{-1}$.

TABLE I

Compounds of formula $I_4$

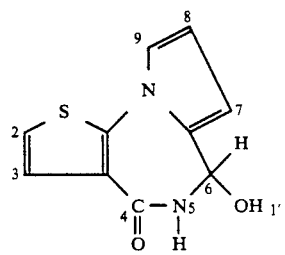

| Compound | Solvent | R$_5$ | H$_2$ (ppm) | H$_3$ (ppm) | H$_7$ (ppm) | H$_8$ (ppm) | H$_9$ (ppm) | NH (ppm) | H$_6$ (ppm) | Other protons (ppm) |
|---|---|---|---|---|---|---|---|---|---|---|
| Example 1 | CDCl$_3$ | —CH$_2$CH$_2$CH$_3$ | 7.36 | 6.96 | 6.00 | 6.28 | 6.96 | 7.06 | 4.96 | CH$_2$: 3.07<br>CH$_2$: 2.46 CH$_3$: 0.90<br>CH$_2$: 1.60 |
| Example 2 | CDCl$_3$ | —CH(CH$_2$)$_2$ (cyclopropyl) | 7.38 | 6.96 | 6.05 | 6.29 | 6.96 | 6.50 | 4.96 | CH$_2$: 3.22<br>CH: 1.96<br>2CH$_2$: 1.10 and 0.98 |
| Example 3 | CDCl$_3$ | —CH$_2$CH$_2$—C$_6$H$_5$ | 7.34 | 6.92 | 5.98 | 6.26 | 6.92 | 6.73 | 4.95 | CH$_2$: 3.03<br>CH$_2$: 2.86<br>CH$_2$: 2.82 |
| Example 4 | CDCl$_3$ | —C$_6$H$_4$—CH$_3$ (para) | 7.32 | 6.92 | 6.05 | 6.27 | 6.97 | 6.70 | 5.11 | CH$_2$: 3.58<br>CH$_3$: 2.42<br>C$_6$H$_4$: 7.84 and 7.26 |
| Example 5 | CDCl$_3$ | —C$_6$H$_4$—CH$_3$ (ortho) | 7.31 | 6.95 | 6.04 | 6.27 | 6.95 | 7.02 | 5.10 | CH$_2$: 3.58<br>CH$_3$: 2.48<br>C$_6$H$_4$: 7.68, 7.40, 7.28 |
| Example 6 | CDCl$_3$ | —C$_6$H$_3$(OCH$_3$)$_2$ | 7.37 | 6.95 | 6.05 | 6.30 | 6.96 | 6.50 | 5.13 | CH$_2$: 3.66<br>C$_6$H$_3$: 7.29, 7.06 and 6.95<br>2CH$_3$: 3.80 and 3.78 |
| Example 7 | DMSO-d$_6$ | —C$_6$H$_4$—Cl | 7.35 | 7.00 | 6.23 | 6.23 | 7.35 | 8.20 | 4.80 | CH$_2$: 3.67<br>C$_6$H$_4$Cl: 8.10, 8.0, 7.60 |
| Example 8 | CDCl$_3$ | —(2-thienyl) | 7.37 | 6.97 | 6.10 | 6.29 | 6.97 | 6.59 | 5.13 | CH$_2$: 3.55<br>C$_4$H$_3$S: 7.73 and 7.16 |

TABLE I-continued
Compounds of formula $I_A$

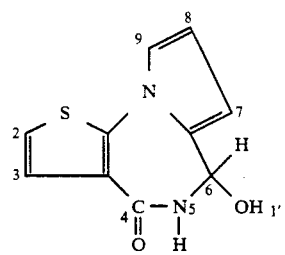

| Compound | Solvent | $R_5$ | $H_2$ (ppm) | $H_3$ (ppm) | $H_7$ (ppm) | $H_8$ (ppm) | $H_9$ (ppm) | NH (ppm) | $H_6$ (ppm) | Other protons (ppm) |
|---|---|---|---|---|---|---|---|---|---|---|
| Example 9 | CDCl$_3$ | 4-F-C$_6$H$_4$— | 7.35 | 6.93 | 6.07 | 6.29 | 6.93 | 6.45 | 5.19 | CH$_2$: 3.55<br>C$_6$H$_4$F: 7.91, 6.93 and 7.15 |
| Example 10 | CDCl$_3$ | furyl | 7.38 | 6.98 | 6.09 | 6.29 | 6.98 | 6.47 | 5.11 | CH$_2$: 3.48<br>C$_4$H$_3$O: 7.26, 7.38 and 6.51 |
| Example 11 | CDCl$_3$ | —C(CH$_3$)$_3$ | 7.38 | 6.93 | 6.03 | 6.28 | 6.96 | 6.13 | 4.98 | CH$_2$: 3.11<br>3CH$_3$: 1.54 |

TABLE II
Compounds of formula $I_B$

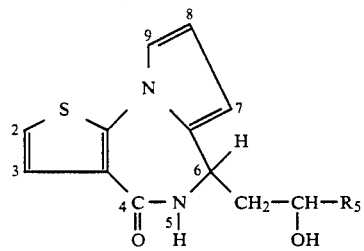

| Compound | Solvent | $R_5$ | $H_2$ (ppm) | $H_3$ (ppm) | $H_7$ (ppm) | $H_8$ (ppm) | $H_9$ (ppm) | NH (ppm) | $H_6$ (ppm) | Other protons (ppm) |
|---|---|---|---|---|---|---|---|---|---|---|
| Example 13 | CDCl$_3$ | —CH$_2$CH$_2$CH$_3$ | 7.34 | 6.92 | 6.04 | 6.27 | 6.92 | 7.03 | 4.66 | CH: 4.04<br>OH: 2.40 CH$_3$: 0.94<br>CH$_2$: 2.10<br>CH$_2$: 1.50 and 1.34 |
| Example 14 | CDCl$_3$ | cyclopropyl-CH— | 7.37 | 6.94 | 6.06 | 6.31 | 6.94 | 7.07 | 4.70 | CH: 3.29 OH: 2.40<br>CH$_2$: 2.28<br>CH: 1.04<br>CH$_2$: 0.58 and 0.31 |
| Example 15 | CDCl$_3$ | C$_6$H$_5$— | 7.34 | 6.93 | 6.09 | 6.30 | 6.33 | 7.34 | 5.17 | CH$_2$: 2.37<br>CH: 4.62<br>C$_6$H$_5$: 7.34 |
| Example 17 | DMSO-d$_6$ | —CH(CH$_3$)$_2$ | 7.20 | 7.08 | 6.09 | 6.26 | 7.08 | 8.13 | 4.46 | OH: 4.52<br>CH: 3.64<br>CH$_2$: 2.88 2CH$_3$: 0.88<br>CH: 1.90 |

TABLE II-continued
Compounds of formula $I_B$

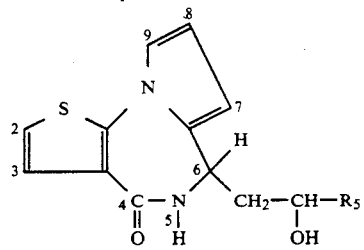

| Compound | Solvent | | $H_2$ (ppm) | $H_3$ (ppm) | $H_7$ (ppm) | $H_8$ (ppm) | $H_9$ (ppm) | NH (ppm) | $H_6$ (ppm) | Other protons (ppm) |
|---|---|---|---|---|---|---|---|---|---|---|
| Example 18 | $CDCl_3$ | (2,5-dimethoxyphenyl) | 7.38 | 6.94 | 6.14 | 6.31 | 6.94 | 6.74 | 5.36 | OH: 4.70 OH: 2.56 $2CH_3$: 3.81 $CH_2$: 2.38 $C_6H_3$: 7.07 and 6.81 |

TABLE III
Compounds of formula $I_C$

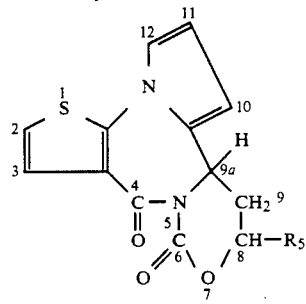

| Compound | Solvent | $R_5$ | $H_2$ (ppm) | $H_3$ (ppm) | $H_{10}$ (ppm) | $H_{11}$ (ppm) | $H_{12}$ (ppm) | $H_8$ (ppm) | $H_{9a}$ (ppm) | $CH_2$'9 | Other protons (ppm) |
|---|---|---|---|---|---|---|---|---|---|---|---|
| Example 19 | $CFCl_3$ | $-CH_3$ | 7.36 | 7.36 | 6.40 | 6.52 | 7.36 | 5.00 | 5.15 | CH: 2.54 CH: 2.31 | $CH_3$: 1.42 |
| Example 20 | $CDCl_3$ | $-CH_2CH_2CH_3$ | 7.37 | 7.37 | 6.41 | 6.48 | 7.35 | 4.84 | 5.15 | CH: 2.71 CH: 2.35 | $CH_2$: 1.68 and 1.45 $CH_3$: 0.94 |
| Example 21 | $CDCl_3$ | (4-methylphenyl) | 7.26 | 7.26 | 6.22 | 6.32 | 7.26 | 5.30 | 4.50 | 2.52 | $CH_3$: 2.32 $C_6H_4$: 8.59, 7.40, 7.26 |

TABLE IV
Compounds of formula $I_D$

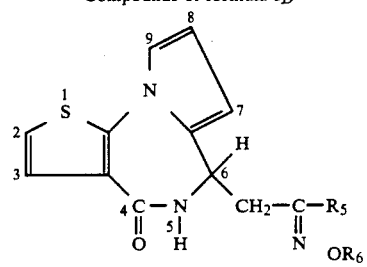

| Compound | Solvent | $R_6$ | $R_5$ | $H_2$ (ppm) | $H_3$ (ppm) | $H_7$ (ppm) | $H_8$ (ppm) | $H_9$ (ppm) | NH | $H_6$ | Other protons (ppm) |
|---|---|---|---|---|---|---|---|---|---|---|---|
| Example 22 | $CDCl_3$ | H | $-CH_3$ | 7.40 | 7 | 6.37 | 6.13 | 7.0 | 7.89 | 4.57 | OH: 10.72 $CH_2$: 2.89 $CH_3$: 1.93 |

TABLE IV-continued

Compounds of formula I$_D$

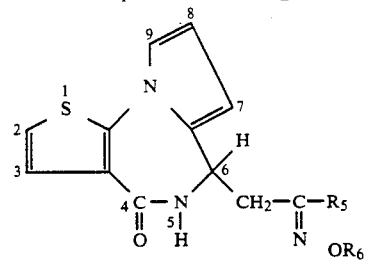

| Compound | Solvent | R$_6$ | R$_5$ | H$_2$ (ppm) | H$_3$ (ppm) | H$_7$ (ppm) | H$_8$ (ppm) | H$_9$ (ppm) | NH | H$_6$ | Other protons (ppm) |
|---|---|---|---|---|---|---|---|---|---|---|---|
| Example 23 | CDCl$_3$ | H | —CH(CH$_3$)$_2$ | 7.40 | 6.94 | 6.34 | 6.17 | 6.98 | 7.67 | 4.57 | OH: 9.63<br>CH$_2$: 2.55<br>CH: 3.66<br>2CH$_3$: 1.10 |
| Example 24 | CDCl$_3$ | H | —CH(CH$_2$)$_2$ (cyclopropyl) | 7.40 | 6.95 | 6.34 | 6.16 | 7.00 | 7.40 | 4.88 | OH: 4.88<br>CH: 1.49<br>2CH$_2$: 0.75 |
| Example 25 | CDCl$_3$ | H | CH$_2$CH$_2$CH$_3$ | 7.40 | 6.95 | 6.34 | 6.14 | 6.97 | 7.50 | 4.6 | CH$_2$: 2.9<br>CH$_2$: 1.50 and 1.19<br>CH$_3$: 0.90 |
| Example 26 | CDCl$_3$ | H | C$_6$H$_5$ (phenyl) | 7.33 | 6.95 | 6.29 | 6.07 | 6.95 | 6.63 | 5.15 | CH$_2$: 3.62<br>C$_6$H$_5$: 7.95, 7.59, 7.47 |
| Example 27 | CDCl$_3$ | H | p-CH$_3$-C$_6$H$_4$ | 7.33 | 6.90 | 6.38 | 6.28 | 7.00 | 10.76 | 4.55 | CH$_2$: 4.12 and 3.13<br>CH$_3$: 2.33<br>C$_6$H$_4$: 7.55 and 7.13 |
| Example 28 | CDCl$_3$ | CH$_3$ | —CH(CH$_2$)$_2$ (cyclopropyl) | 7.30 | 6.88 | 6.26 | 6.02 | 6.92 | 6.64 | 4.90 | CH: 1.24<br>2CH$_2$: 0.92 and 0.88<br>CH$_3$: 3.84 |
| Example 29 | DMSO-d$_6$ | CH$_3$ | —CH$_3$ | 7.28 | 7.21 | 6.28 | 6.22 | 7.13 | 8.14 | 4.61 | CH$_3$: 3.71<br>CH$_3$: 1.75 |

TABLE V

Compounds of formula I$_E$

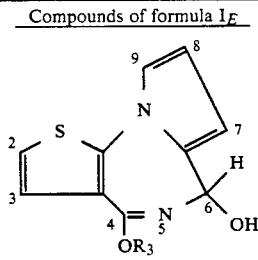

| Compound | Solvent | R$_3$ | H$_2$ (ppm) | H$_3$ (ppm) | H$_7$ (ppm) | H$_8$ (ppm) | H$_9$ (ppm) | H$_6$ (ppm) | OH (ppm) | Other protons (ppm) |
|---|---|---|---|---|---|---|---|---|---|---|---|
| Example 30 | DMSO-d$_6$ | —CH$_3$ | 7.30 | 7.14 | 6.34 | 6.34 | 7.10 | 5.60 | 6.18 | CH$_2$: 3.70 |
| Example 31 | DMSO-d$_6$ | —CH$_2$CH$_3$ | 7.31 | 7.14 | 6.2 | 6.2 | 7.11 | 5.60 | 6.20 | CH$_2$: 4.16<br>CH$_3$: 1.10 |
| Example 32 | DMSO-d$_6$ | —CH$_2$CH$_2$CH$_3$ | 7.31 | 7.15 | 6.30 | 6.30 | 7.10 | 5.66 | 6.30 | CH$_2$: 4.08<br>CH$_2$: 1.63<br>CH$_3$: 0.95 |
| Example 33 | DMSO-d$_6$ | —CH$_2$CH=CH$_2$ | 7.33 | 7.16 | 6.20 | 6.20 | 7.10 | 5.63 | 6.20 | CH: 5.93<br>CH$_2$: 4.63<br>CH$_2$: 5.21 |

TABLE VI

Compounds of formula $I_F$

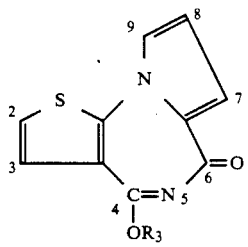

| Compound | Solvent | $R_3$ | $H_2$ (ppm) | $H_3$ (ppm) | $H_7$ (ppm) | $H_8$ (ppm) | $H_9$ (ppm) | Other protons (ppm) |
|---|---|---|---|---|---|---|---|---|
| Example 34 | DMSO-$d_6$ | —CH$_3$ | 7.43 | 7.30 | 7.08 | 6.63 | 7.70 | CH$_3$: 3.93 |
| Example 35 | DMSO-$d_6$ | —CH$_2$CH$_3$ | 7.40 | 7.30 | 7.01 | 6.60 | 7.65 | CH$_2$: 4.35; CH$_3$: 1.34 |
| Example 36 | DMSO-$d_6$ | —CH$_2$CH$_2$CH$_3$ | 7.45 | 7.31 | 7.08 | 6.65 | 7.68 | CH$_2$: 4.31; CH$_2$: 1.78; CH$_3$: 1.00 |

TABLE VII

Compounds of formula $I_G$

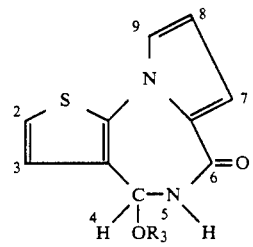

| Compound | Solvent | $R_3$ | $H_2$ (ppm) | $H_3$ (ppm) | $H_7$ (ppm) | $H_8$ (ppm) | $H_9$ (ppm) | NH (ppm) | $H_4$ (ppm) | Other protons (ppm) |
|---|---|---|---|---|---|---|---|---|---|---|
| Example 37 | CDCl$_3$ | —CH$_3$ | 7.26 | 6.93 | 6.93 | 6.40 | 7.17 | 7.31 | 5.25 | CH$_3$: 3.35 |
| Example 38 | DMSO-$d_6$ | —CH$_2$CH$_3$ | 7.25 | 7.11 | 6.97 | 6.37 | 7.37 | 9.05 | 5.32 | CH$_2$: 3.48; CH$_3$: 0.98 |
| Example 39 | DMSO-$d_6$ | —CH$_2$CH$_2$CH$_3$ | 7.25 | 7.11 | 6.95 | 6.35 | 7.36 | 9.03 | 5.32 | CH$_2$: 3.39; CH$_2$: 1.36; CH$_2$: 0.65 |

TABLE VIII

Compounds of formula $I_H$

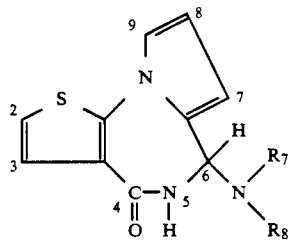

Solvent used: CDCl$_3$

| Compound | $R_7$ (ppm) | $R_8$ (ppm) | $H_2$ (ppm) | $H_3$ (ppm) | $H_7$ (ppm) | $H_8$ (ppm) | $H_9$ (ppm) | NH (ppm) | $H_6$ (ppm) | Other protons (ppm) |
|---|---|---|---|---|---|---|---|---|---|---|
| Example 41 | H | —CH$_3$ | 7.39 | 6.91 | 6.19 | 6.31 | 6.98 | 6.81 | 5.03 | CH$_3$: 1.75 |
| Example 42 | H | —CH$_2$CH$_3$ | 7.34 | 6.92 | 6.19 | 6.31 | 6.98 | 6.76 | 5.15 | CH$_2$: 2.82; CH$_3$: 1.11 |
| Example 43 | H | —CH$_2$CH$_2$CH$_3$ | 7.39 | 6.91 | 6.18 | 6.31 | 6.98 | 6.52 | 5.13 | CH$_2$: 2.73; CH$_2$: 1.49; CH$_3$: 0.88; NH: 4.82 |

TABLE VIII-continued

Compounds of formula I$_H$

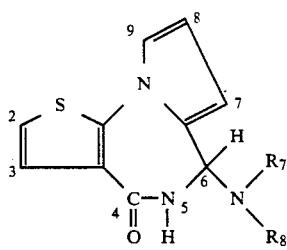

Solvent used: CDCl$_3$

| Compound | R$_7$ (ppm) | R$_8$ (ppm) | H$_2$ (ppm) | H$_3$ (ppm) | H$_7$ (ppm) | H$_8$ (ppm) | H$_9$ (ppm) | NH (ppm) | H$_6$ (ppm) | Other protons (ppm) |
|---|---|---|---|---|---|---|---|---|---|---|
| Example 44 | H | —CH(CH$_3$)$_2$ | 7.38 | 6.92 | 6.17 | 6.31 | 6.97 | 6.83 | 5.20 | CH: 3.08<br>2CH$_3$: 1.07 |
| Example 45 | —CH$_3$ | —CH$_3$ | 7.38 | 6.85 | 6.21 | 6.29 | 6.99 | 6.28 | 4.46 | 2CH$_3$: 2.20 |
| Example 46 | —CH$_2$CH$_3$ | —CH$_2$CH$_3$ | 7.37 | 6.89 | 6.19 | 6.31 | 6.98 | 6.31 | 5.11 | 2CH$_2$: 2.66<br>2CH$_2$: 0.98 |
| Example 47 | pyrrolidine | | 7.37 | 6.83 | 6.19 | 6.27 | 6.97 | 6.71 | 4.64 | CH$_2$: 2.64<br>CH$_2$: 2.35<br>2CH$_2$: 1.65 |
| Example 48 | piperidine | | 7.35 | 6.85 | 6.18 | 6.28 | 6.97 | 6.62 | 4.65 | CH$_2$: 2.63<br>CH$_2$: 2.19<br>3CH$_2$: 1.39 |
| Example 49 | morpholine | | 7.35 | 6.86 | 6.22 | 6.29 | 7.00 | 6.93 | 4.53 | 2CH$_2$: 3.47<br>CH$_2$: 2.50<br>CH$_2$: 2.14 |
| Example 50 | N-COC$_2$H$_5$ piperazine | | 7.35 | 6.85 | 6.18 | 6.28 | 6.97 | 6.67 | 4.65 | 2X CH$_2$: 3.24<br>2X CH$_2$: 2.48<br>CH$_2$: 4.07<br>CH$_3$: 1.21 |
| Example 51 | —H | phenyl | 7.18 | 7.18 | 6.38 | 6.32 | 7.16 | 8.85 | 5.71 | ar CH: {7.19, 7.16, 6.78}<br>NH: 6.62 |
| Example 52 | —H | CH$_2$-phenyl | 7.29 | 6.90 | 6.18 | 6.30 | 6.97 | 6.48 | 5.12 | CH$_2$: 3.93<br>ar CH: 7.29<br>CH$_2$: 1.6 |

TABLE IX

Compounds of formula $I_J$

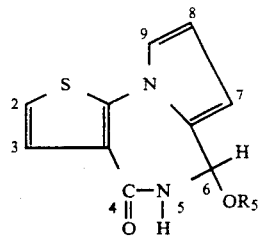

| Compound | Solvent | R$_5$ | H$_2$ (ppm) | H$_3$ (ppm) | H$_7$ (ppm) | H$_8$ (ppm) | H$_9$ (ppm) | HH (ppm) | H$_6$ (ppm) | Other protons (ppm) |
|---|---|---|---|---|---|---|---|---|---|---|
| Example 55 | CDCl$_3$ | —CH(CH$_3$)$_2$ | 7.38 | 6.86 | 6.25 | 6.29 | 7.06 | 7.06 | 5.52 | CH: 3.79 <br> 2CH$_3$: 1.71 |
| Example 56 | CDCl$_3$ | —CH$_2$C$_6$H$_5$ | 7.41 | 6.88 | 6.23 | 6.29 | 7.03 | 7.53 | 5.44 | CH$_2$: 4.53 <br> C$_6$H$_5$: 7.20, 7.31, 7.20 |

TABLE X

Compounds of formula $I_K$

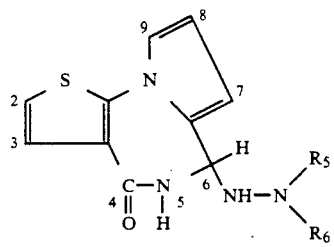

| Compound | Solvent | R$_5$ (ppm) | R$_6$ (ppm) | H$_2$ (ppm) | H$_3$ (ppm) | H$_7$ (ppm) | H$_8$ (ppm) | H$_9$ (ppm) | NH (ppm) | H$_6$ (ppm) | Other protons (ppm) |
|---|---|---|---|---|---|---|---|---|---|---|---|
| Example 57 | CDCl$_3$ | —CH$_3$ | —CH$_3$ | 7.48 | 7.21 | 6.53 | 6.79 | 6.94 | 5.52 | 5.15 | 2CH$_3$: 2.74 <br> NH: 5.33 |
| Example 58 | CDCl$_3$ | —H | —C$_6$H$_5$ | 7.56 | 7.18 | 6.64 | 6.71 | 6.80 | 6.43 | 5.33 | NH: 5.33 <br> NH: 6.38 <br> C$_6$H$_5$: 7.18, 7.12, 7.18, 6.70 |
| Example 59 | DMSO | —H | 2,4-(NO$_2$)$_2$C$_6$H$_3$ | 8.00 | 7.08 | 6.28 | 6.28 | 7.19 | 9.94 | 5.54 | NH: 5.85 <br> NH: 8.79 <br> C$_6$H$_3$: 7.30 and 8.79 |

TABLE XI

Compounds of formula $I_L$

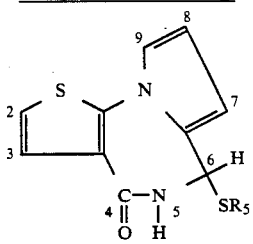

| Compound | Solvent | $R_5$ (ppm) | $H_2$ (ppm) | $H_3$ (ppm) | $H_7$ (ppm) | $H_8$ (ppm) | $H_9$ (ppm) | NH (ppm) | $H_6$ (ppm) | Other protons (ppm) |
|---|---|---|---|---|---|---|---|---|---|---|
| Example 60 | CDCl$_3$ | CH$_2$CO$_2$CH$_3$ | 7.40 | 6.92 | 6.28 | 6.28 | 7.04 | 6.92 | 5.94 | CH$_2$: CH: 3.29 CH: 3.06 CH$_3$: 3.76 |
| Example 61 | CDCl$_3$ | C$_6$H$_5$ | 7.43 | 6.95 | 6.11 | 6.26 | 7.02 | 6.60 | 5.73 | C$_6$H$_5$: 7.34 |
| Example 62 | DMSO | CH$_2$CH$_2$CO$_2$H | 7.21 | 7.21 | 6.31 | 6.31 | 7.21 | 9.11 | 5.73 | CH$_2$: 2.43 and 2.60 OH: 12.21 |
| Example 63 | DMSO | CH$_2$CH$_2$CONH$_2$ | 7.25 | 7.25 | 6.27 | 6.27 | 7.25 | 9.00 | 5.68 | NH$_2$: 7.27 and 6.73 CH$_2$: 2.56 and 2.24 |

TABLE XII

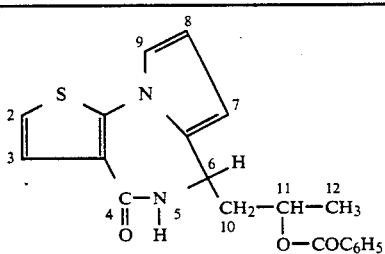

| Compound | $H_2$ (ppm) | $H_3$ (ppm) | $H_7$ (ppm) | $H_8$ (ppm) | $H_9$ (ppm) | NH (ppm) | $H_6$ (ppm) | $H_{10}$ (ppm) | $H_{11}$ (ppm) | $H_{12}$ (ppm) | Other protons (ppm) |
|---|---|---|---|---|---|---|---|---|---|---|---|
| Example 64 | 7.35 | 6.93 | 6.10 | 6.16 | 6.93 | 7.40 | 5.15 | 2.27 | 4.44 | 1.32 | ar CH: 7.24 7.40 7.90 |

TABLE XIII

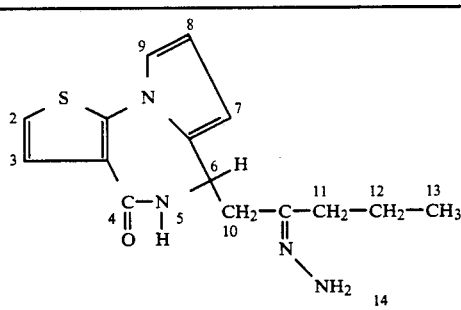

| Compound | $H_2$ (ppm) | $H_3$ (ppm) | $H_7$ (ppm) | $H_8$ (ppm) | $H_9$ (ppm) | $H_5$ (ppm) | $H_6$ (ppm) | $H_6$ (ppm) | $H_{11}$ (ppm) | $H_{12}$ (ppm) | $H_{12}$ (ppm) | $H_{12}$ (ppm) |
|---|---|---|---|---|---|---|---|---|---|---|---|---|
| Example 65 | 7.27 | 7.21 | 6.11 | 6.27 | 7.11 | 7.91 | 4.64 | 2.74 | 2.10 | 1.44 | 0.88 | 5.76 |

EXAMPLE 66

Affinity for cholecystokinin receptors

The affinity of the compounds of formula (I) for cholecystokinin receptors was studied by determining the median inhibitory concentration (IC$_{50}$) for the binding of iodine-125-labeled cholecystokinin to the receptors of rat pancreas plasma membranes (SD males, IFFA CREDO, 200–225 g) and to the receptors of guinea pig brain membranes (males, COB LABO, 325–350 g), according to the protocol described by INNIS R. B. and SNYDER S. M., Euro. J. Pharmacol., 65, 123–124, 1980.

The IC$_{50}$ values found for the receptors of rat pancreas plasma membranes were, for the majority of the compounds, between 0.01 and 60 nM/l, and the IC$_{50}$ values found for the receptors of guinea pig brain membranes between 350 and 30,000 nM/l. The ratios of the $IC_{50}$ in relation to the pancreatic receptors to the $IC_{50}$ in relation to the brain receptors were found to be between 3 and 20,000.

EXAMPLE 67

Activity in respect of cholecystokinin in vivo

The antagonist activity of the compounds of formula (I) in respect of CCK was determined in mice (SWISS male, 18–20 g) in the gastric evacuation model described by LOTTI V. J. et al. (LIFE SCIENCES, 39; 1631–1638; 1986), by determining the 50% effective dose ($ED_{50}$) which protects the animals against the inhibition of gastric evacuation induced by sulfated CCK-8 (80 μg/kg, s.c.). The values obtained in the gastric evacuation test were 0.032–0.290 mg/kg.

EXAMPLE 68

Acute hypoxia in mice

Male CD1 mice (Charles RIVER) which have received the test compound intraperitoneally 30 minutes beforehand are subjected to an acute hypoxia of the hypobaric type. For this purpose, they are placed in a chamber in which the atmospheric pressure can be lowered rapidly (in the space of 30 seconds) to a value of 160 mbar, thereby causing the death of all the animals approximately 15 seconds after this hypoxic pressure is obtained.

Survival of the brain is assessed by measuring the time of appearance of the last gasp of breath. The survival time of a treated batch is compared with that of a control batch receiving only the solvent.

The results of this study demonstrated that the compounds of the invention are active at a dose of 3 mg/kg and above. In this case, an approximately 30–40% increase in the survival of the animals is observed. For a dose of 100 mg/kg, some compounds of the invention increase the survival time of the animals up to 200%.

EXAMPLE 69

| Hard gelatin capsules containing 5 mg of 5,6-dihydro-6-[2-hydroxy-2-(4-methylphenyl)ethyl]-4-oxo-4H-pyrrolo[1,2-a]thieno[3,2-f][1,4]diazepine(compound of Example 16): | |
|---|---|
| Compound of Example 16 | 5 mg |
| Corn starch | 20 mg |
| Lactose | 30 mg |
| Talc | 10 mg |
| Per No. 3 hard gelatin capsule. | |

We claim:
1. A compound of general formula (I):

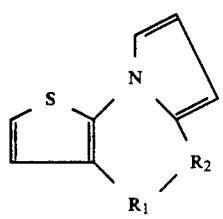
(I)

in which:
$R_1$ represents a radical of general formula ($Z_0$), ($Z_1$), ($Z_2$), ($Z_3$) or ($Z_4$)

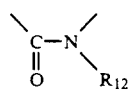
($Z_0$)

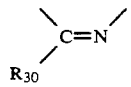
($Z_1$)

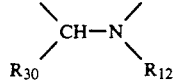
($Z_2$)

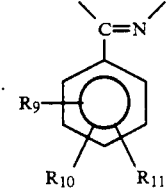
($Z_3$)

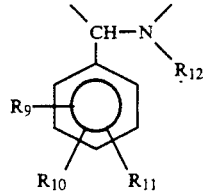
($Z_4$)

in which formulae:
$R_3$ represents a hydrogen atom or a linear or branched alkyl or alkenyl radical having 1 to 6 carbon atoms, $R_9$, $R_{10}$ and $R_{11}$, which may be identical or different, each represent a hydrogen atom, a halogen atom or an alkyl radical having 1 to 6 carbon atoms, $R_{12}$ represents a hydrogen atom or, with $R_2$ and the nitrogen atom to which they are attached, forms a radical of general formula (W):

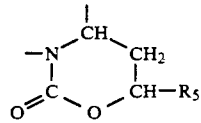
(W)

$R_2$ represents a methylene radical, a hydroxymethylene radical, a carbonyl radical or a radical of general formula ($Y_1$), ($Y_2$), ($Y_3$) or ($Y_4$):

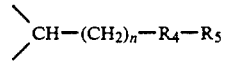
($Y_1$)

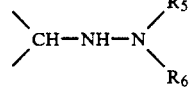
($Y_2$)

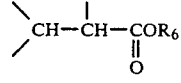
($Y_3$)

-continued

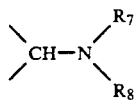
(Y4)

or, with $R_{12}$ and the nitrogen atom to which they are attached, forms a radical of general formula (W):

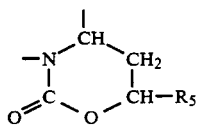
(W)

in which formulae:

$R_4$ represents an oxygen or sulfur atom, a carbonyl radical or a radical of general formula $(X_1)$, $(X_2)$, $(X_3)$ or $(X_4)$:

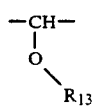
($X_1$)

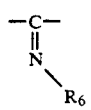
($X_2$)

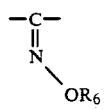
($X_3$)

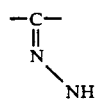
($X_4$)

n is between 0 and 4 inclusive, $R_5$ represents a hydrogen atom, a linear or branched alkyl chain having 1 to 10 carbon atoms, optionally interrupted by one or more oxygen or sulfur atoms, a phenyl or benzoyl radical or an phenylalkyl or naphthylalkyl radical having 7 to 11 carbon atoms (optionally substituted on the aromatic ring with one or more halogen atoms, linear or branched alkyl radicals having 1 to 6 carbon atoms, nitro radicals or linear or branched alkoxy radicals having 1 to 6 carbon atoms), a linear or branched carboxyalkyl radical having 2 to 7 carbon atoms, a linear or branched alkoxycarbonylalkyl radical having 3 to 10 carbon atoms, a linear or branched alkoxycarbonyl radical having 2 to 7 carbon atoms, a linear or branched carbamoylalkyl radical having 2 to 7 carbon atoms, a cycloalkyl radical having 3 to 7 carbon atoms, an unsaturated ring-system selected from thienyl, furyl, pyrrolyl, pyridinyl, and pyrimidinyl, pyridylcarbonyl or pyrimidinylcarbonyl radical, a clofibroyl radical or a 6-hydroxy-2,5,7,8-tetramethylchroman-2-carbonyl radical, $R_6$ represents a hydrogen atom or a linear or branched alkyl radical having 1 to 6 carbon atoms, $R_7$ and $R_8$, which may be identical or different, each represent a hydrogen atom, a linear of branched alkyl radical having 1 to 6 carbon atoms, a phenyl radical or a phenylalkyl radical having 7 to 9 carbon atoms (optionally substituted on the aromatic ring with one or more halogen atoms or alkyl or alkoxy groups having 1 to 6 carbon atoms), or, together with the nitrogen atom to which they are attached form a saturated or unsaturated 5- to 7-membered ring-system comprising 1 to 2 hetero atoms selected from nitrogen, oxygen and sulfur, optionally substituted with an alkylcarbonyl of 2-5 carbon atoms or alkoxycarbonyl group having 2 to 5 carbon atoms, $R_{13}$ represents a hydrogen atom, a linear or branched alkylcarbonyl radical having 2 to 6 carbon atoms or a benzoyl radical, with the provisos that:
when $R_1$ represents a radical of general formula ($Z_3$), then $R_2$ cannot represent a methylene radical,
when $R_1$ represents a radical of general formula ($Z_0$) and $R_{12}$ represents a hydrogen atom, then $R_2$ cannot represent the following radicals:

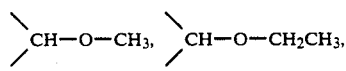

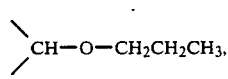

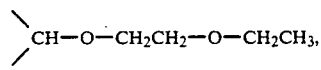

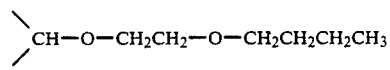

when $R_1$ represents a radical of general formula ($Z_0$), $R_{12}$ represents a hydrogen atom and $R_2$ represents a radical of general formula ($Y_1$) with n=1 and $R_4$ representing a carbonyl radical, then $R_5$ cannot represent a methyl, isopropyl or phenyl radical,
when $R_1$ represents a radical of general formula ($Z_0$) and $R_{12}$ represents a hydrogen atom, then $R_2$ cannot represent a carbonyl radical,
its isomers, diastereoisomers and enantiomers,
its addition salts with a pharmaceutically acceptable inorganic or organic acid.

2. A compound, as claimed in claim 1, of general formula ($I_A$):

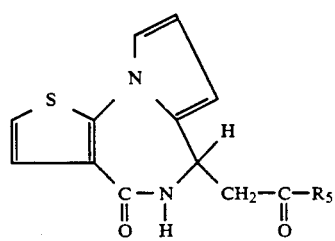
($I_A$)

in which $R_6$ has the same meaning as in claim 1, as well as its isomers isolated or in the form of a mixture.

3. A compound, as claimed in claim 1, of general formula ($I_B$):

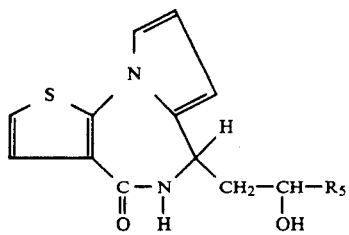

in which $R_6$ has the same meaning as in the claim 1, as well as its isomers isolated or in the form of a mixture.

4. A compound, as claimed in claim 1, of general formula ($I_C$):

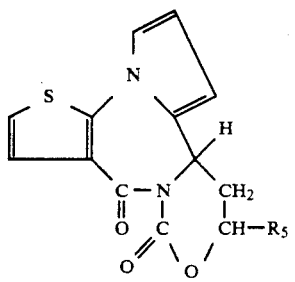

in which $R_5$ has the same meaning as in the claim 1, as well as its isomers isolated or in the form of a mixture.

5. A compound, as claimed in claim 1, of general formula ($I_D$):

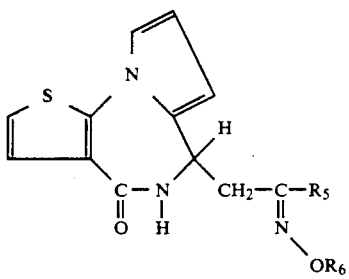

in which $R_5$ and $R_6$ have the same meaning as in the claim 1, as well as its isomers isolated or in the form of a mixture.

6. A compound, as claimed in claim 1, of general formula ($I_E$):

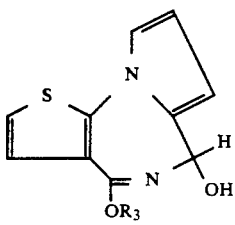

in which $R_3$ has the same meaning as in the claim 1, as well as its isomers isolated or in the form of a mixture.

7. A compound, as claimed in claim 1, of general formula ($I_F$):

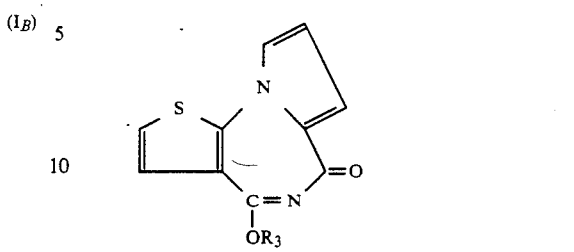

in which $R_3$ has the same meaning as in the claim 1, as well as its isomers isolated or in the form of a mixture.

8. A compound, as claimed in claim 1, of general formula ($I_G$):

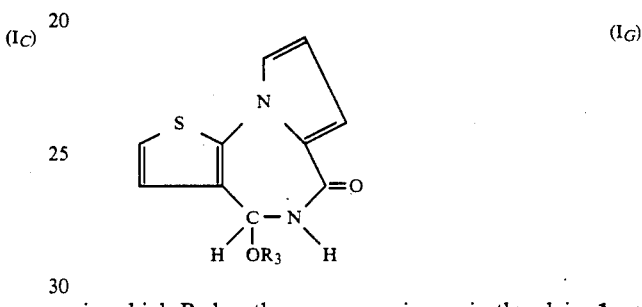

in which $R_3$ has the same meaning as in the claim 1, as well as its isomers isolated or in the form of a mixture.

9. A compound, as claimed in claim 1, of general formula ($I_H$):

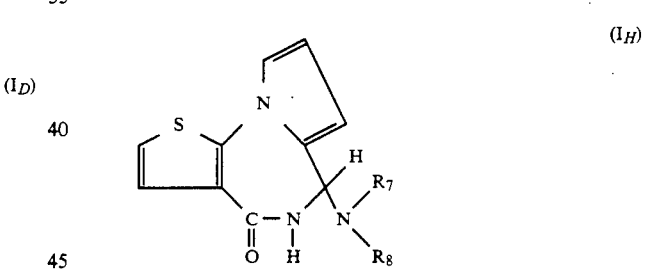

in which $R_7$ and $R_8$ have the same meaning as in the claim 1, as well as its isomers isolated or in the form of a mixture, and their addition salt with a pharmaceutically acceptable acid.

10. A compound, as claimed in claim 1, of general formula ($I_J$):

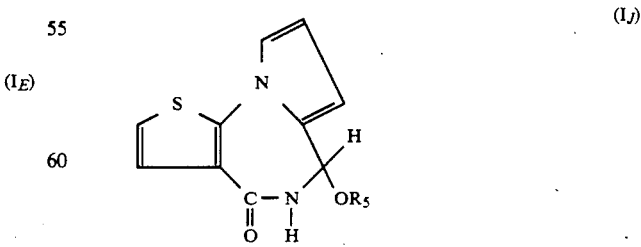

in which $R_5$ has the same meaning as in the claim 1, as well as its isomers isolated or in the form of a mixture.

11. A compound, as claimed in claim 1, of general formula ($I_K$):

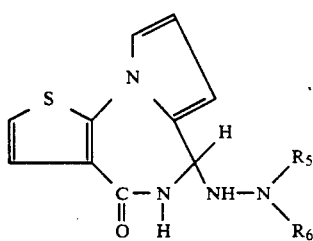

in which $R_5$ and $R_6$ have the same meaning as in the claim 1, as well as its isomers isolated or in the form of a mixture, and their addition salt with a pharmaceutically acceptable acid.

12. A compound, as claimed in claim 1, of general formula $(I_L)$:

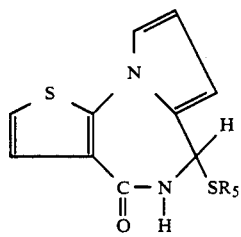

in which $R_5$ has the same meaning as in the claim 1, as well as its isomers isolated or in the form of a mixture.

13. The compound as claimed in the claim 1 which is 5,6-dihydro-6-(2-benzyloxypropyl)-4-oxo-4H-pyrrolo[1,2-a]thieno [3,2-f][1,4]diazepine, as well as its isomers isolated or in the form of a mixture.

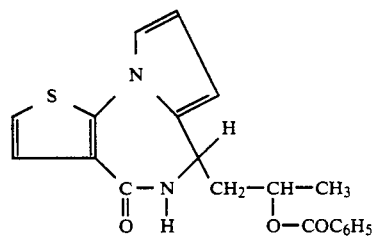

14. The compound as claimed in the claim 1 which is 5,6-dihydro-6-(2-hydrazono-1-pentyl)-4-oxo-4H-pyrrolo [1,2-a]thieno [3,2-f][1,4]diazepine, as well as its isomers isolated or in the form of a mixture, and their addition salts with a pharmaceutically acceptable acid.

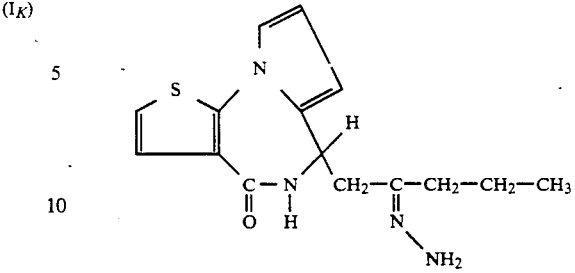

15. The compound as claimed in the claim 1 which is 5,6-dihydro-6-hydroxy-4-oxo-4H-pyrrolo[1,2-a]thieno[3,2-f][1,4]diazepine, as well as its isomers isolated or in the form of a mixture.

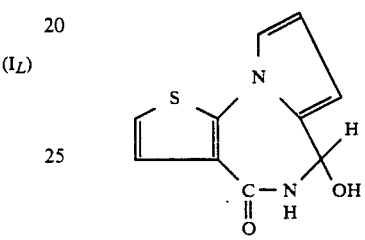

16. The compound as claimed in the claim 1 which is 5,6-dihydro-4-oxo-4H-pyrrolo[1,2-a]thieno[3,2-f][1,4diazepine.

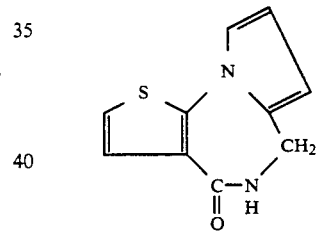

17. A pharmaceutical composition containing as active principle an effective amount of a compound of claims 1 to 16, alone or in combination with one or more pharmaceutically acceptable, non-toxic, inert vehicles or excipients.

18. A method for treating a living animal body afflicted with stroke, cerebral aging or metabolic diseases including hyperlipidemia, hypertriglyhyperglycemia comprising the step of administering to the said living animal an amount of a compound of claim 1 which is suitable for the alleviation of the said condition.

* * * * *

UNITED STATES PATENT AND TRADEMARK OFFICE
CERTIFICATE OF CORRECTION

PATENT NO. : 5,190,939
DATED : March 2, 1993
INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Title Page, [54]: Title should read --PYRROLO (1,2-a) THIENO (3,2-f) (1,4) DIAZEPINES--
Title Page, [*], second line: "Jul. 8," should read --Jul. 14,--
Title Page, [54] Abstract, second column, second formula: "$R_{30}$" should read --$R_3O$--
Title Page, [54] Abstract, second column, third formula: "$R_{30}$" should read --$R_3O$--
Col. 1, line 1: Title should read --PYRROLO (1,2-a) THIENO (3,2-f) (1,4)--
Col. 2, ($Z_1$) Compound: "$R_{30}$" should read --$R_3O$--
Col. 2, ($Z_2$) Compound: "$R_{30}$" should read --$R_3O$--
Col. 5, ($I_A$) Compound:

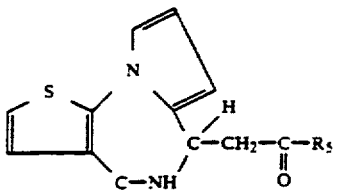     should read     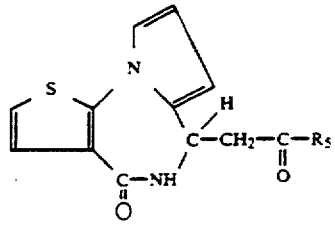

Col. 5, line 68: "($I_H$)" should read --($I_M$)--
Col. 15, line 13: Insert the following new paragraph: --Melting point: 174° C. (Ethyl ether), yellow crystals.--
Col. 15, line 52: Insert a comma between "1485" and "1430"
Col. 17, line 40: "dihydro-2-" should read --dihydro-6-(2- --
Col. 19, line 21: "thiene" should read --thieno--
Col. 21, line 61: Insert the following after the word "is": --drained, washed with water, dried and recrystallized.--

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Col. 24, line 51: Insert --[3,2-f]-- before "[1,4]diazepine"
Col. 25, line 4: "[3,2-f]1,4]diazepine" should read --[3,2-f][1,4]diazepine--
Col. 25, line 47: "5.6-dihydro" should read --5,6-dihydro--
Col. 26, line 41: Insert the following new paragraph: --Yield: 85%.--
Col. 27, line 58: Insert the word --100-- after the word "in".
Col. 28, line 11: Insert the word --60-- after the word "in".
Col. 29, line 5: "9" should read --g--.
Col. 29, line 6: "sin9le" should read --single--.
Col. 31, line 22: Insert the following: --Process A--
Col. 31, line 42: "ior" should read --for--
Col. 33, line 34: Insert the word --in-- before the word "Example".
Col. 34, line 5: Insert --[3,2-f] after the word "thieno".
Col. 34, line 6: "]diazeoin" should read --]diazepin--
Col. 34, line 27: Second column of the table under "C %", second line, first number to the right of the word "Found": "50225" should read --50.25--
Col. 35-36, Table I: First formula:

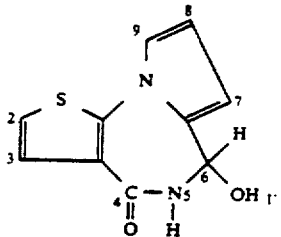 should read 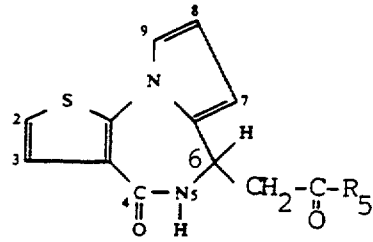

UNITED STATES PATENT AND TRADEMARK OFFICE
CERTIFICATE OF CORRECTION

PATENT NO. : 5,190,939
DATED : March 2, 1993
INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Col. 37-38, Table I-continued: First formula:

Col. 37-38, Table I-continued, Example 10, last column of figures, second line: "$C_4H_3O:7.26$" should read --$C_4H_3O:7.62$--
Col. 37-38, Table II, in the heading: Insert --$R_5$-- in the third column of the heading.
Col. 37-38, Table II, Example 13: Delete the "$R_5$_" in the third column.
Col. 37-38, Table II, Example 14, sixth column of figures: "6.06" should read --6.09--
Col. 37-38, Table II, Example 15, second column of figures: Delete the "R_" in the third column.
Col. 37-38, Table II, Example 17, last column of figures, second line: "CH: 3.64" should read --CH: 3.46--
Col. 39-40, Table II-cont., below the formula in the heading of the Table, in the third column: Insert --$R_5$--
Col. 39-40, Table III, Example 19, second column: "$CFCl_3$" should read --$CDCl_3$--
Col. 39-40, Table IV, 10th and 11th columns of the heading line, second line: --(ppm)-- should be added under "NH" and "$H_6$"
Col. 41-42, Table IV-continued, 10th and 11th columns of the heading line, second line: --(ppm)-- should be added under "NH" and "$H_6$".

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Col. 49-50, Table XIII, 9th column of the heading line, first line: the second "$H_6$" should be --$H_{10}$--
Col. 51, line 54: Insert the words --selected from those-- after the word "compound" and delete the word "general".
Col. 51, line 67: Delete the word "general".
Col. 52, Formula ($Z_1$): "$R_{30}$" should read --$R_3O$--
Col. 52, Formula ($Z_2$): "$R_{30}$" should read --$R_3O$--
Col. 52, line 35: Delete the words "a" (both occurrences), "atom", and "linear or".
Col. 52, line 36: Delete the words "branched" and "radical"
Col. 52, line 39: Delete the words "a" (both occurrences) and "atom" (both occurrences)
Col. 52, line 40: Delete the words "an" and "radical"
Col. 52, line 41: Delete the words "a" and "atom"
Col. 52, line 43: Delete the word "general"
Col. 52, line 52: Delete the words "a" (both occurrences) and "radical".
Col. 52, line 53: Delete the word "a" before "carbonyl", delete the word "radical" (2nd occurrence), delete "gen-", and insert a comma after the word "carbonyl",
Col. 52, line 54: Delete "eral".
Col. 53, line 9: Delete the word "general"
Col. 53, line 19: Delete the words "an", "atom", and "a".
Col. 53, line 20: Delete the words "radical" (1st occurrence), and "general"
Col. 53, line 43: Delete the words "between" and "and", and insert the word --to-- after the number "0".
Col. 53, line 44: Delete the words "a" (both occurrences), "atom", and "linear or branched".
Col. 53, line 45: Delete the word "chain"

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

| | |
|---|---|
| Col. 53, line 46: | Delete the words "one or more" and "atoms" |
| Col. 53, line 47: | Delete the words "a", "radical" and "an" |
| Col. 53, line 48: | Delete the word "radical" and insert a comma after the word "atoms" |
| Col. 53, line 49: | Delete the "(" |
| Col. 53, line 50: | Delete the words "one or more" and "atoms, linear or branched" |
| Col. 53, line 51: | Delete the word "radicals" and insert a comma after the word "nitro" |
| Col. 53, line 52: | Delete the words "radicals or linear", "branched", and "radicals" |
| Col. 53, line 53: | Delete the words ")", and "a linear or branched" |
| Col. 53, line 54: | Delete the word "a" |
| Col. 53, line 55: | Delete the words "linear or branched" and "radical" |
| Col. 53, line 56: | Delete the words "a linear or branched" |
| Col. 53, line 57: | Delete the word "radical" |
| Col. 53, line 58: | Delete the words "a linear or branched" and "radical" |
| Col. 53, line 59: | Delete the words "a" and "radical" |
| Col. 53, line 63: | Delete the word "radical" (both occurrences) and the word "a" (both occurrences) |
| Col. 53, line 64: | Delete the word "radical" |
| Col. 53, line 65: | Delete the word "a" before the word "hydrogen", delete the word "atom" and delete "a linear or" |
| Col. 53, line 66: | Delete the words "branched" and "radical" |
| Col. 53, line 68: | Delete the word "a" before the word "hydrogen", delete the word "atom" and delete "a linear of branched" |
| Col. 54, line 1: | Delete the words "radical" and "a" |

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

| | |
|---|---|
| Col. 54, line 2: | Delete the words "radical" (both occurrences) and "a" |
| Col. 54, line 3: | Insert a comma after the word "atoms" and delete the "(" |
| Col. 54, line 4: | Delete the words "one or more" and "atoms" |
| Col. 54, line 5: | Delete the word "groups" and the ")" |
| Col. 54, line 7: | Insert a comma after the word "attached" |
| Col. 54, line 10: | Delete the word "an" |
| Col. 54, line 11: | Delete the word "group" |
| Col. 54, line 13: | Delete the words "a", "atom", and "a linear or branched" |
| Col. 54, line 14: | Delete the word "radical" |
| Col. 54, line 15: | Delete the words "a" and "radical" |
| Col. 54, line 17: | Delete the word "general" |
| Col. 54, line 18: | Delete the words "a" and "radical" |
| Col. 54, line 19: | Delete the word "general" |
| Col. 54, line 20: | Delete the words "a" and "atom" |
| Col. 54, line 42: | Delete the word "general" |
| Col. 54, line 43: | Delete the words "a" and "atom" |
| Col. 54, line 44: | Delete the word "general" |
| Col. 54, line 45: | Delete the words "a" and "radical" |
| Col. 54, line 46: | Delete the words "a" and "radical" |
| Col. 54, line 47: | Delete the word "general" |
| Col. 54, line 48: | Delete the words "a" and "atom" |
| Col. 54, line 49: | Delete the words "a" and "radical" |
| Col. 54, line 50: | Insert the word --and-- after "enantiomers," |
| Col. 54, line 51: | Insert a dash between the words "pharmaceutically" and "acceptable" |
| Col. 54, line 67: | "$R_6$" should read --$R_5$--, delete the words "as well", and insert the word --or-- at the end of the line |
| Col. 54, line 68: | Delete the word "as" |

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

| | |
|---|---|
| Col. 55, line 15: | "$R_6$" should read --$R_5$--, delete the words "the" (second occurrence), "as", and insert the word --or-- at the end of the line |
| Col. 55, line 16: | Delete the words "well as" |
| Col. 55, line 33: | Delete the word "the" (second occurrence), and replace the word "as" with the word --or-- |
| Col. 55, line 34: | Delete the words "well as" |
| Col. 55, line 50: | Delete the word "the" (second occurrence) |
| Col. 55, line 51: | Delete the words "as well as" and replace them with the word --or-- |
| Col. 55, line 67: | Delete the word "the" (second occurrence), and replace the word "as" with the word --or-- |
| Col. 55, line 68: | Delete the words "well as" |
| Col. 56, line 15: | Delete the word "the" (second occurrence), and replace the word "as" with the word --or-- |
| Col. 56, line 16: | Delete the words "well as" |
| Col. 56, line 31: | Delete the word "the" (second occurrence), and replace the word "as" with the word --or-- |
| Col. 56, line 32: | Delete the words "well as" |
| Col. 56, line 47: | Delete the word "the" |
| Col. 56, line 48: | Delete the words "as well as" and replace them with the word --or-- |
| Col. 56, line 49: | Delete the words "and their" and replace them with the word --or an-- |
| Col. 56, line 50: | Insert a dash between the words "cally" and "acceptable" |

UNITED STATES PATENT AND TRADEMARK OFFICE
CERTIFICATE OF CORRECTION

PATENT NO. : 5,190,939         Page 8 of 10

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

| | |
|---|---|
| Col. 56, line 65: | Delete the word "the" (second occurrence), and replace the word "as" with the word --or-- |
| Col. 56, line 66: | Delete the words "well as" |
| Col. 57, line 13: | Delete the word "the" (second occurrence) |
| Col. 57, line 14: | Delete the words "as well as" and replace with the word --or-- |
| Col. 57, line 15: | Delete the words "and their" and replace with the words --or an-- |
| Col. 57, line 16: | Insert a dash between the words "cally" and "acceptable" |
| Col. 57, line 32: | Delete the word "the" (second occurrence), and replace the word "as" with the word --or-- |
| Col. 57, line 33: | Delete the words "well as" |
| Col. 57, line 34: | Change the first "The" to the word --A-- and delete the word "the" (second occurrence) |
| Col. 57, line 36: | Delete the words "as well as" and replace with the word --or-- |
| Col. 57, line 51: | Change the first "The" to the word --A-- and delete the word "the" (second occurrence) |
| Col. 57, line 53: | Insert the following after the word "diazepine", --having the below formula-- and delete the words "as well as" and replace with the word --or-- |
| Col. 57, line 54: | Delete the words "and their" and replace with the words --or an-- |
| Col. 57, line 55: | "salts" should read --salt--, and insert a dash between the words "pharmaceutically" and "acceptable" |
| Col. 58, line 14: | Change the first "The" to the word --A-- and delete the word "the" (second occurrence) |

UNITED STATES PATENT AND TRADEMARK OFFICE
CERTIFICATE OF CORRECTION

PATENT NO. : 5,190,939
DATED : March 2, 1993
INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Col. 58, line 16: Insert the following after the word "diazepine", --having the below formula-- and delete the words "as well as" and replace with the word --or--

Col. 58, second formula:

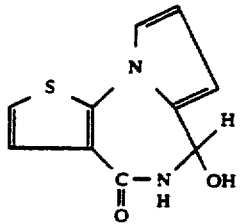  should read  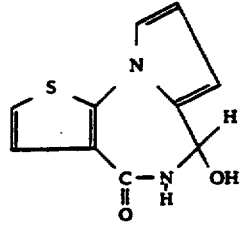

Col. 58, line 30: Change the first "The" to the word --A-- and delete the word "the" (second occurrence)

Col. 58, line 32: "f][1,4diazepine" should read --f][1,4]diazepine-- and insert the following after the word "diazepine", --having the below formula,--

Col. 58, third formula:

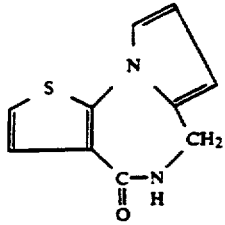  should read  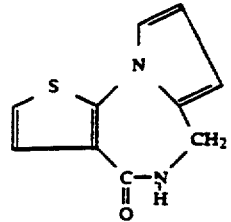

Col. 58, line 47: "non-toxio" should read --non-toxic--
Col. 58, line 49: Delete the word "body"

UNITED STATES PATENT AND TRADEMARK OFFICE
CERTIFICATE OF CORRECTION

PATENT NO. : 5,190,939

DATED : March 2, 1993

INVENTOR(S) : Sylvain Rault, Michel Boulouard, Patrick Dallemagne, Max Robba, Beatrice Guardiola, Michelle Devissaguet It is certified that error appears in the above-indentified patent and that said Letters Patent is hereby corrected as shown below:

Col. 58, line 50: Insert a comma after the word "aging", insert the word --a-- after the word "or", insert the word --ailment-- after the word "metabolic" and cancel the word "diseases"

Col. 58, line 51: Delete the words "including hyperlipidemia, hypertriglyhyperglycemia"

Col. 58, line 53: Insert the words --any of-- after the word "of" (second occurrence), change "claim" to --claims--, and change "1" to --1 through 16--

Signed and Sealed this

Thirteenth Day of June, 1995

Attest:

BRUCE LEHMAN

Attesting Officer

Commissioner of Patents and Trademarks